United States Patent [19]
Kratoska et al.

[11] Patent Number: 6,090,072
[45] Date of Patent: Jul. 18, 2000

[54] EXPANDABLE INTRODUCER SHEATH

[75] Inventors: William F. Kratoska, Plymouth; Sew-Wah Tay, Plymouth; Scott P. Thome, Waite Park; Peter T. Keith, Fridley, all of Minn.

[73] Assignee: SciMed Life Systems, Inc., Maple Grove, Minn.

[21] Appl. No.: 08/615,066

[22] Filed: Mar. 14, 1996

Related U.S. Application Data

[63] Continuation of application No. 08/269,631, Jul. 1, 1994, abandoned, which is a continuation of application No. 07/961,372, Oct. 15, 1992, abandoned.

[51] Int. Cl.⁷ .................................................. A61M 25/00
[52] U.S. Cl. .......................... 604/164; 604/264; 604/280
[58] Field of Search .................................... 604/171, 172, 604/164, 166, 280, 264

[56] References Cited

U.S. PATENT DOCUMENTS

| | | | |
|---|---|---|---|
| 3,509,883 | 5/1970 | Dibelius | 128/348 |
| 3,788,318 | 1/1974 | Kim et al. | 128/214.4 |
| 4,401,433 | 8/1983 | Luther . | |
| 4,411,655 | 10/1983 | Schreck | 604/165 |
| 4,451,256 | 5/1984 | Weiki et al. | 604/164 |
| 4,580,573 | 4/1986 | Quinn | 128/657 |
| 4,589,868 | 5/1986 | Dretler | 604/96 |
| 4,668,221 | 5/1987 | Luther | 604/164 |
| 4,710,181 | 12/1987 | Fuqua | 604/280 |
| 4,738,666 | 4/1988 | Fuqua | 604/280 |
| 4,740,207 | 4/1988 | Kreamer | 623/1 |
| 4,781,681 | 11/1988 | Sharrow et al. | 604/280 |
| 4,781,703 | 11/1988 | Walker et al. | 604/264 |
| 4,795,426 | 1/1989 | Jones | 604/51 |
| 4,846,812 | 7/1989 | Walker et al. | 604/264 |
| 4,921,479 | 5/1990 | Grayzel | 604/164 |
| 4,994,027 | 2/1991 | Farrell | 604/53 |
| 4,994,047 | 2/1991 | Walker et al. | 604/280 |

(List continued on next page.)

FOREIGN PATENT DOCUMENTS

| | | |
|---|---|---|
| 0 420 993 A1 | 4/1991 | European Pat. Off. . |
| 0 546 712 A2 | 11/1992 | European Pat. Off. . |

OTHER PUBLICATIONS

"Spiral Exchange Cannula for the Occluded Drainage Catheter" (A. H. McCain et al), Radiology, vol. 157, pp. 543–544 (1985).

"Replacing the Occluded Percutaneious Nephrostomy Catheter" (R. L. Baron et al), Radiology, vol. 141, p. 824 (1981).

"An Alternative Method for Repair of a Leaking Arterial Chemotherapy Infusion Catheter" (J. L. Burkhalter et al), Journal of Surgical Oncology, vol. 34, pp. 27–28 (1987).

"A Technique for Exchanging a Clotted Intravascular Catheter Using the Original Arteriopuncture Site" (M. L. Skolnick), American Journal of Roentgenology, vol. 109, No. 1, pp. 152–154 (May 1970).

*Primary Examiner*—Todd E. Manahan
*Attorney, Agent, or Firm*—Kinney & Lange, P.A.

[57] ABSTRACT

The present invention comprises a method and device for providing an expandable introducer sheath. The method of employing the inventive device comprises inserting an elongate flexible tubular sheath into a vessel (with a proximal end of the sheath extending proximally outward through the skin), to slidably receive intravascular devices. When a larger size introducer sheath is desired, the sheath is manipulated while still in the vessel to expand its inner diameter to a larger size. In one embodiment, the sheath is made of a shape-memory polymer and is manipulated by inserting a heated mandrel (with an outer diameter larger than the inner diameter of the sheath) within the sheath to cause the sheath to expand to an inner diameter at least approximately equal to an outer diameter of the mandrel. The shape-memory polymer material ensures that the sheath will retain its expanded inner diameter. Alternatively, the sheath is formed from a telescoping multi-tubular arrangement of progressively larger tubes. In any case, insertion of the inventive sheath into the skin requires only a single small puncture which is then only expanded as needed while the sheath remains in place.

30 Claims, 9 Drawing Sheets

U.S. PATENT DOCUMENTS

| | | | |
|---|---|---|---|
| 5,015,238 | 5/1991 | Solomon et al. | 604/164 |
| 5,015,239 | 5/1991 | Browne | 604/164 |
| 5,019,090 | 5/1991 | Pinchuk | 606/194 |
| 5,035,686 | 7/1991 | Crittenden et al. | 604/96 |
| 5,061,254 | 10/1991 | Karakelle et al. | 604/265 |
| 5,066,285 | 11/1991 | Hillstead | 604/164 |
| 5,089,005 | 2/1992 | Harada | 606/194 |
| 5,092,839 | 3/1992 | Kipperman | 604/53 |
| 5,139,511 | 8/1992 | Gill et al. | 606/198 |
| 5,158,545 | 10/1992 | Trudell et al. | 604/53 |
| 5,167,634 | 12/1992 | Corrigan, Jr. et al. | 604/160 |
| 5,176,659 | 1/1993 | Manciini | 604/280 |
| 5,183,464 | 2/1993 | Dubrul et al. | 128/3 |
| 5,201,756 | 4/1993 | Horzewski et al. | 604/264 |
| 5,234,425 | 8/1993 | Fogarty et al. . | |

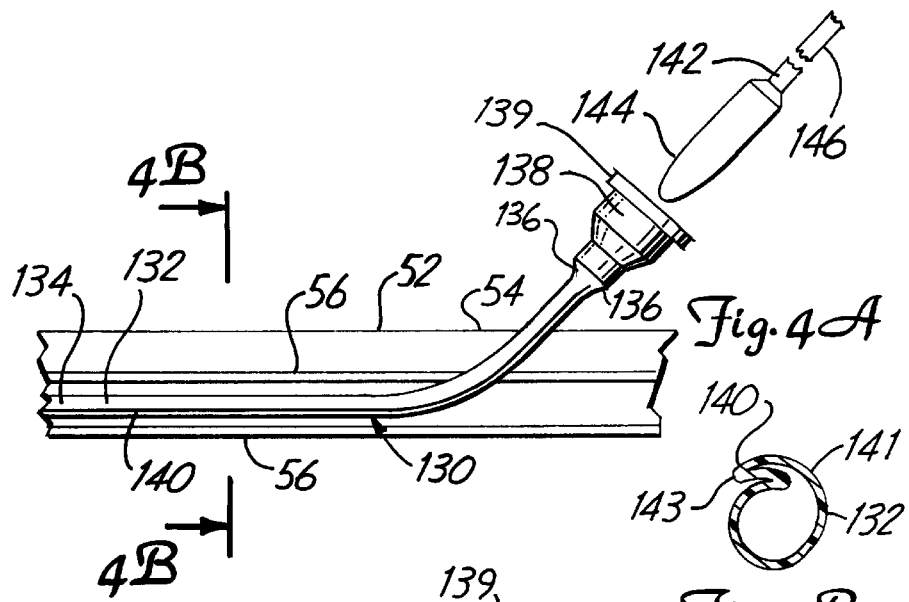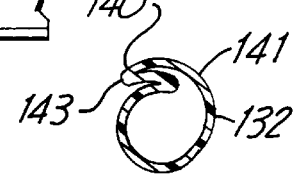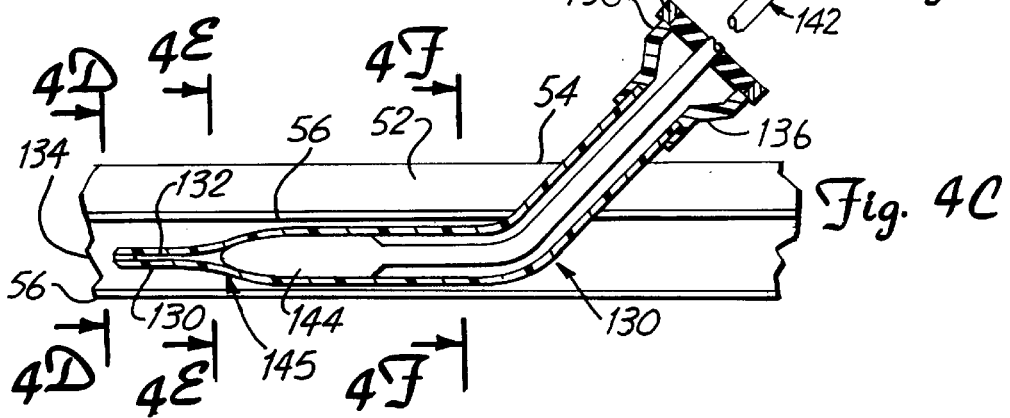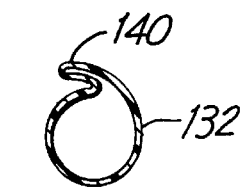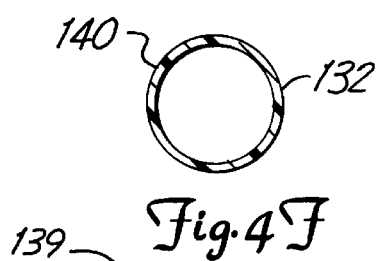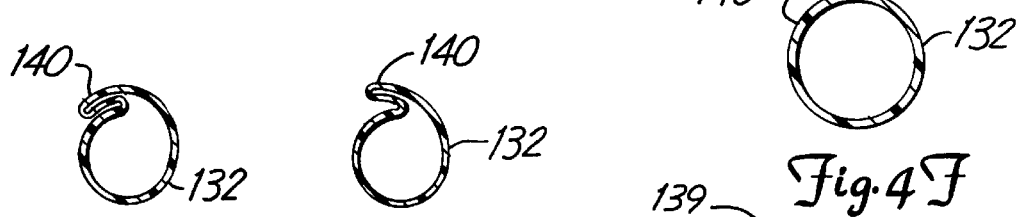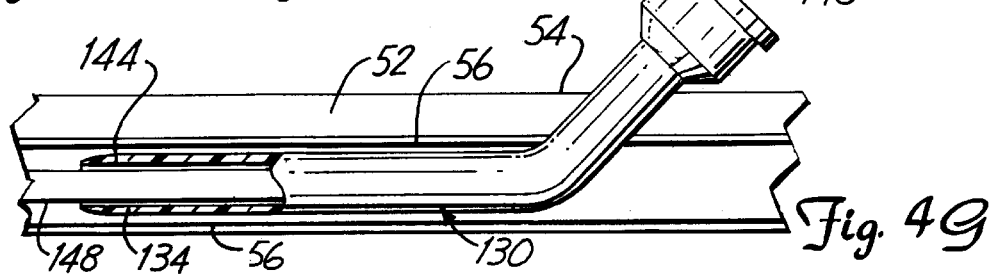

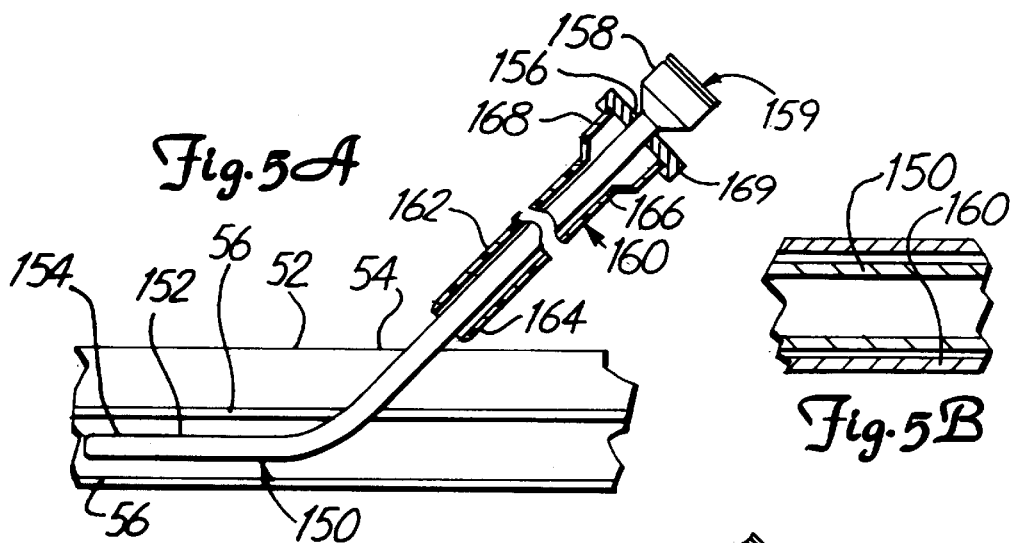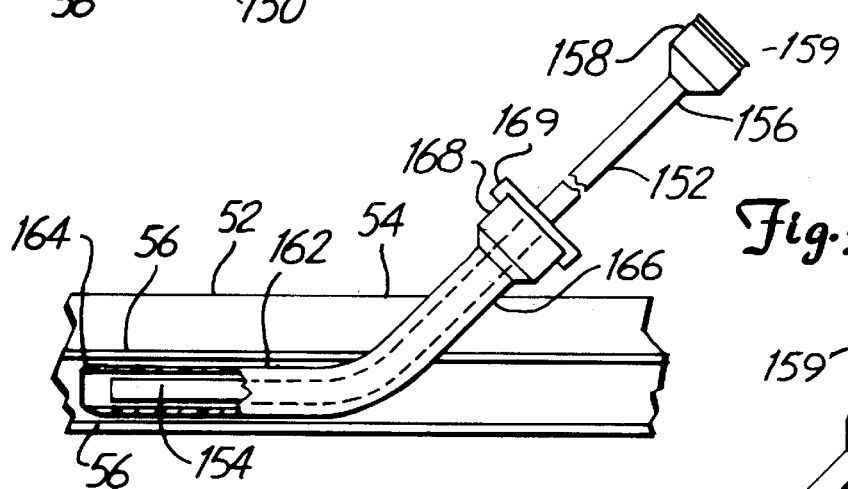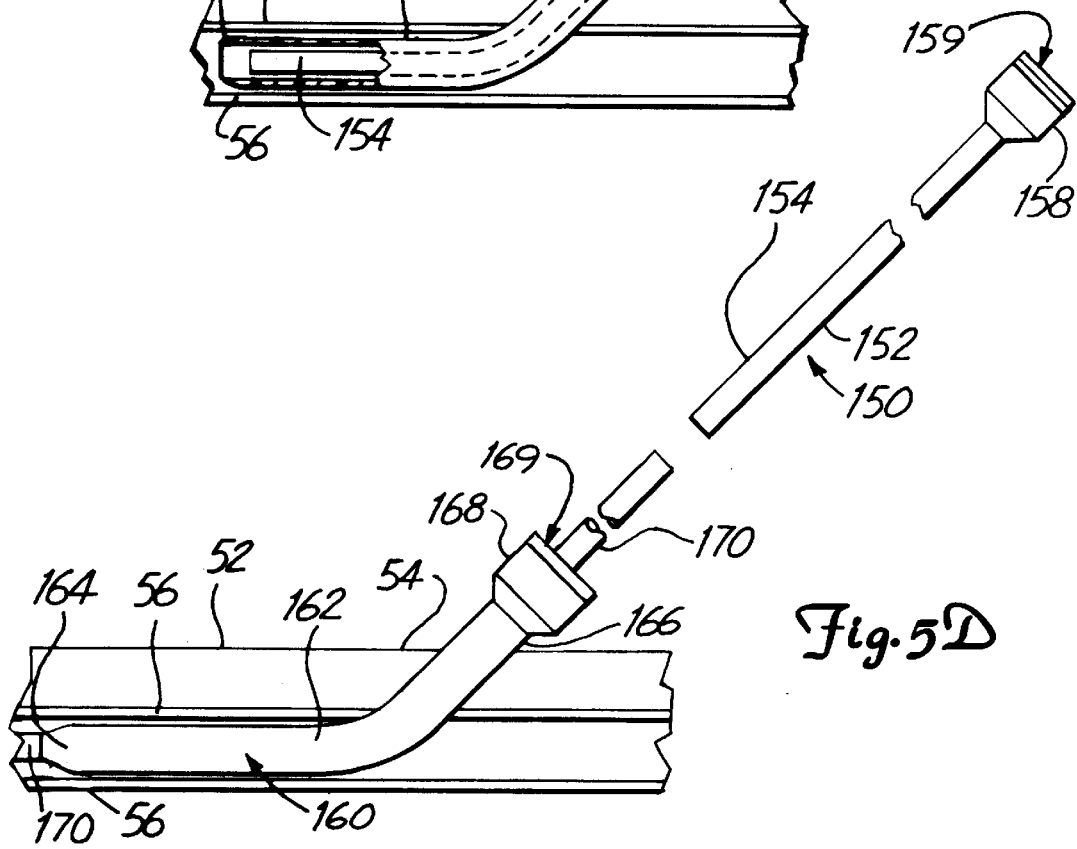

EXPANDABLE INTRODUCER SHEATH

This is a Continuation of application Ser. No. 08/269,631, filed Jul. 1, 1994, now abandoned, which is a continuation of application Ser. No. 07/961,372 filed Oct. 15, 1992, now abandoned.

BACKGROUND OF THE INVENTION

The present invention relates to the field of sheaths for introducing intravascular catheters. In particular, the present invention relates to a flexible sheath for percutaneously introducing intravascular catheters such as an angioplasty catheter.

Angioplasty has gained wide acceptance in recent years as an efficient and effective method for treating various types of vascular diseases. In particular, angioplasty is widely used for opening stenoses in the coronary arteries, although it is also used for treatment of stenoses in other parts of the vascular system.

The most widely used form of angioplasty makes use of an introducer sheath positioned at the entry point of the intravascular catheters into the cardiovascular system. For instance, the distal end of the introducer sheath is inserted into the femoral artery located in the groin of the patient and pushed distally through the artery until the sheath is firmly seated within the artery. The proximal end of the introducer sheath protrudes outside of the patient's body to provide an entryway for subsequent insertion of additional or other intravascular devices. The additional or other intravascular devices include guide catheters, guide wires, and balloon dilatation catheters, or angiographic catheters as well as other therapeutic and diagnostic intravascular catheters.

The introducer sheath typically is inserted into the vessel through the skin percutaneously. Prior to the development of percutaneous insertion method, entry into the vessel was achieved by cutting the skin with a scalpel to expose the vessel of interest and then inserting a needle or other puncture apparatus through the vessel wall to facilitate entry of the introducer sheath and/or an intravascular catheter. In the percutaneous insertion technique, a needle or similar puncture device is inserted into the skin without first cutting the skin to expose the vessel. The needle is then advanced through the skin (and tissue) until the needle enters the vessel of interest.

In the common percutaneous insertion procedure, a distal end of a hollow thin-walled puncture needle (alternatively, a Seldinger needle may be used) is inserted through the skin (and underlying tissue) and through a wall of the desired vessel. A proximal end of the needle remains outside of the surface of the skin. Next, a distal end of a thin flexible wire is inserted into the proximal end of the needle and advanced therethrough until a distal end of the wire extends distally beyond the distal end of the needle and into the vessel. A proximal end of the wire remains outside, extending through the proximal end of the needle. While maintaining the flexible wire in position within the vessel, the needle is proximally withdrawn over the wire until completely removed from the vessel and the skin (and underlying tissue).

Next, the physician prepares an introducer sheath outside the patient's body by inserting a distal end of a dilator (e.g., an elongate flexible cylinder with a bore extending therethrough) into a proximal end of the flexible plastic introducer sheath and advances the dilator therethrough. The dilator is advanced until a distal tip portion of the dilator extends distally beyond a distal end of the sheath and a proximal portion of the dilator remains outside of the proximal end of the sheath. The distal tip portion of the dilator has a tapered outer diameter that gradually increases proximally to an enlarged diameter adjacent the distal end of the sheath. By means of a snap fit or friction fit, the proximal portion of the dilator is releasably secured to the proximal portion of the sheath so that the dilator and sheath comprise an assembled unit for insertion into the vessel.

The distal end of the dilator (with the sheath loaded thereon) is threaded over the proximal end of the wire and inserted through the skin (and underlying tissue) and into the vessel by distally advancing the dilator and sheath over the wire. Because the dilator is longer than the sheath, the distal end of the dilator enters the vessel before the distal end of the sheath and the dilator and sheath are advanced together until the distal portion of the sheath extends within the vessel. The tapered distal tip portion of the dilator gradually expands the opening in the vessel wall as the dilator moves there through. With the distal end of the sheath properly positioned (extending into the vessel), the proximal end of the sheath and the proximal end of the dilator remain outside the surface of the skin. Next, while maintaining the sheath in place within the vessel and after disengaging the dilator from the sheath, the dilator and wire are removed by proximally withdrawing them from inside the sheath. With the sheath in place, the puncture site is now ready for the widely known transluminal angioplasty procedure or other procedure involving intravascular catheters. The sheath provides a convenient and protective entryway for intravascular devices into the cardiovascular system.

In the case of an angioplasty procedure, the next step includes inserting a distal end of a hollow guide catheter through the sheath and into the vessel. A proximal end of the guide catheter remains outside of the proximal end of the sheath for facilitating insertion of intravascular devices through the guide catheter. For instance, a guide wire could be inserted through the guide catheter and advanced distally until a distal end of the guide wire is distal to a stenosis in a coronary artery. A balloon dilatation catheter is then threaded over the proximal end of the guide wire and inserted up through the guide catheter and manipulated to treat a stenosis.

The sheath for introducing the guide catheter and other intravascular devices facilitates the insertion and withdrawal of intravascular devices through the skin and underlying tissue into a vessel. The sheath minimizes trauma to the skin puncture site and vessel wall caused by the frequent insertion and removal of intravascular devices from the vessel. In addition, the introducer sheath prevents backbleeding, i.e., blood flow exiting the punctured vessel, because the typical sheath has a hemostasis valve carried therein at its proximal end. The hemostasis valve forms a fluid tight seal about a variety of sizes of intravascular catheters, guide wires, and the like to prevent a flow of blood out of the patient or air into the patient. The hemostasis valve also sealingly closes when no device extends through the hemostasis valve (and sheath).

Although the inner diameter of the sheath should have a close tolerance with the outer diameter of the intravascular device, it is desirable to have some spacing between the sheath and intravascular device for perfusion or for drug infusion flow techniques through that spacing. A side arm with a 3-way valve connector connected to the proximal end or hub of the sheath can be used for blood perfusion or drug infusion.

Reasons for minimizing the size of a sheath include minimizing the size of the opening in the vessel and the skin puncture site, increasing the stability of the sheath within the skin puncture site, and reducing the time for this puncture site to heal. There are two reasons that this time is of interest. First, ensuring the proper clotting of this opening requires the attention of trained personnel for several minutes (e.g., 15 minutes) after the sheath is removed. Second, patients need to remain immobile for many hours after the sheath is removed to ensure that the clotted opening in the vessel does not reopen. These healing times are so long because patients typically have Heparin®, an anticoagulant, in their cardiovascular systems. It is desirable to reduce both of these times.

Although it is desirable to minimize the outer diameter of the introducer sheath, an intravascular device having an outer diameter larger than the inner diameter of the introducer sheath already in place may be required later in the surgical procedure. These larger size intravascular devices require the use of a larger size introducer sheath and accordingly, necessitate exchanging the first introducer sheath for another introducer sheath having a larger inner diameter.

For example, this situation frequently arises because a smaller size introducer sheath is required for angiography procedures and a larger size introducer sheath is required for an angioplasty procedure. For example, a procedure using angiography catheters typically would be performed with an introducer sheath having a size 5 or 6 French inner diameter. However, present day angioplasty guide catheters (through which a angioplasty dilation catheter would pass) are generally too large to fit through size 5 and 6 French introducer sheaths. Accordingly, if it were determined that an angioplasty procedure were required, then a larger inner diameter size introducer sheath (e.g., 7 or 8 French) would be needed to accommodate the outer diameter of an angioplasty guide catheter. If an adjunctive procedure such as an atherectomy or stent placement procedure would be necessary after or instead of the angioplasty procedure, an even larger size introducer sheath would be required.

With the possibility of these different sized introducer sheaths being required, the physician is faced with a dilemma. It is highly desirable to use the smallest size introducer sheath possible to minimize the size of the opening in the skin and in the vessel (e.g., femoral artery). However, if one selects an introducer sheath that is too small to accommodate all the necessary intravascular devices, then the smaller size introducer sheath would have to be later exchanged for a larger one. Confronted by this choice, physicians commonly choose to insert an introducer sheath of a size large enough to easily accommodate all potential intravascular devices. This means that an introducer sheath frequently is selected that is much larger than necessary and this initial choice for the larger introducer sheath may sacrifice the highly desirable goal of minimizing the size of the opening in the artery wall and skin puncture site.

In a case where a smaller inner diameter size sheath was initially selected and must be removed to be replaced by a larger inner diameter size sheath, all intravascular devices from within the vessel typically must be removed (with the possible exception of a coronary guide wire). Next, the smaller size sheath must be removed from the vessel and skin surface puncture site. To do so, with the sheath still in place within the vessel, the physician reinserts the dilator into the sheath until the dilator extends within the vessel beyond the sheath (and the sheath locks with the dilator) so that the wire may be threaded through the dilator until the distal end of the wire extends through the vessel distally beyond the distal end of the dilator. While leaving the wire in place within the vessel, the dilator and sheath are removed from within the vessel.

Next, to place a larger introducer sheath within the vessel, a physician would repeat the entire percutaneous puncture insertion method for introducer sheaths as previously described (except for not using a puncture needle because the wire already extends the vessel). If this procedure is performed at a new puncture site along the vessel, then a new puncture site would be needed. In any case, repeating the percutaneous insertion procedure traumatizes the endothelium layer of the vessel wall, the surrounding tissue, and the skin much more than performing the percutaneous insertion technique only once. Moreover, many patients receiving angioplasty treatment already suffer from diseased arterial walls which magnifies the problem of repetitious trauma to vessel wall.

Because of the large number of devices of varying sizes which may be used in a combined angiography/angioplasty, or adjunctive procedure, the conventional introducer sheath has many deficiencies. One major deficiency is that there is no mechanism for increasing the size of the introducer sheath (once having been inserted) other than by replacing the smaller size introducer sheath with a second larger size introducer sheath through a second percutaneous insertion procedure. This deficiency drives the physician to reluctantly select an introducer sheath with a size potentially much larger than necessary, needlessly increasing the size and healing time of the opening created in the vessel wall and skin surface. This results, in substantial part, in increased patient recuperation time which typically dictates an overnight stay in the hospital for a procedure that otherwise could be done on an outpatient basis.

Various attempts have been made at solving the problem of having an expandable or variable size introducer device. For example, Grayzel U.S. Pat. No. 4,921,479 is directed to a removable, expandable sheath for introducing catheters. The sheath is made of a semi-stiff plastic with memory and formed in a tubular configuration with a longitudinal slit extending along the entire length of the sheath. The tubular structure is typically coiled about its longitudinal axis so its tubular wall overlaps itself. Upon insertion of a larger diameter intravascular device, the tubular sheath enlarges its inner diameter by uncoiling to the extent necessary to accommodate the catheter inserted therein. The Grayzel device is disadvantageous because the slit extending the length of the sheath permits potential backbleeding and the moveable nature of the walls relative to each other can traumatize the vessel possibly causing a dissection of the vessel wall or at least exacerbating the injury to the endothelium layer of the vessel wall and the skin tissue.

Another attempt includes Schreck U.S. Pat. No. 4,411,655 which relates to an expandable cannula for introducing catheters into the cardiovascular system. The cannula is made of a metallic shape-memory alloy formed into a cylindrical cannula with a plastic sheath covering the cannula. The lumenal diameter of the cannula dilates after insertion into the body vessel as the temperature of the shape-memory alloy is heated by equilibrating to the predetermined body temperature or by application of resistance heating or other methods to activate the shape-memory alloy. This device requires an additional plastic sheath to cover the metal alloy cannula, thereby creating an outer diameter larger than necessary. Moreover, because the cannula is made of a metal alloy, it is inflexible contributing to greater tissue trauma because the cannula will have less "give" when pressing against the surrounding tissue and vessel wall. Moreover, in the embodiment in which the cannula expands because of the temperature of the body, there is no choice for the operator to decide when the cannula expands.

SUMMARY OF THE INVENTION

The present invention comprises a method and device for providing an expandable introducer sheath. The method of employing the inventive device comprises inserting an elongate flexible tubular sheath into a vessel (with a proximal end of the sheath extending proximally outward through the skin), to slidably receive intravascular devices. When a larger size introducer sheath is desired, one manipulates the sheath while still in the vessel to expand its inner diameter to a larger size. In one embodiment, the sheath is made of a shape-memory polymer and the manipulating step may comprise inserting a heated mandrel (with an outer diameter larger than the inner diameter of the sheath) within the sheath to cause the sheath to expand to an inner diameter at least approximately equal to an outer diameter of the mandrel. The shape-memory polymer material ensures that the sheath will retain its expanded inner diameter.

In another embodiment, the elongate flexible tubular sheath is made of a shape-memory polymer and before placement within the vessel, the sheath is mechanically "formed down" to have an inner diameter smaller than the original size inner diameter formed when the sheath was extruded. Once in the vessel, the sheath can be manipulated to expand its inner diameter back to the original size. To do so, a heated mandrel can be inserted into the sheath to cause the sheath to exceed a glass transition temperature of the polymer material and thereby induce the shape-memory polymer material sheath to "snap back" to its original and larger size inner diameter.

Another embodiment of the present invention provides an expandable inner diameter introducer by employing a sheath including a inner sheath tubular portion and an outer sheath coaxially slidable over the inner sheath. The outer sheath is shorter than the inner sheath so that when the inner sheath is disposed within the vessel and extends proximally outward therefrom, the outer sheath is coaxially disposed about the inner sheath proximal to a skin surface. To provide an expanded inner diameter introducer sheath, the outer sheath is advanced distally over the inner sheath until within the vessel. Then, while maintaining the outer sheath in the vessel, the inner sheath is withdrawn proximally from within the outer sheath. The outer sheath which remains in the vessel provides an expanded or larger inner diameter introducer sheath.

Of course, in addition to other preferred embodiments described further in the detailed description, many other embodiments are contemplated which provide an expandable introducer sheath of the present invention.

The expandable introducer sheath of the present invention facilitates convenient percutaneous insertion and removal of intravascular devices. The present invention provides an introducer sheath capable of being expanded to have a larger inner diameter when desired without removal of the sheath from within the vessel (and while a coronary guide wire remains in the artery). This significantly reduces trauma to the skin tissue and punctured vessel (e.g., femoral artery wall) of a patient because it alleviates the need to completely remove a smaller introducer sheath from within the vessel in exchange for a larger inner diameter sheath to be inserted percutaneously in the injurious conventional multi-step manner. The sheath is flexible which further reduces trauma to the skin and vessel wall because the sheath can "give" and/or "flex" when in contact with these body tissues. The polymeric sheath material also reduces the likelihood of thrombogenic activity. The sheath is of simple tubular construction having a continuous wall surface along its length and hub region. This increases the ease of handling the sheath and accentuates blood flow management while reducing a chance of dissecting or injuring the vessel wall because the continuous smooth surface of the sheath lacks discontinuities (e.g., longitudinal free edges and sharp corners like those in the previous devices).

More importantly, an expandable introducer sheath diminishes a physicians pre-operative dilemma of wanting to use the smallest size introducer sheath to minimize puncture site trauma yet selecting a size large enough to accommodate all the necessary intravascular devices so that the chosen introducer sheath does not have to be later exchanged for a larger size sheath. With the present invention, a physician can percutaneously insert a smaller inner diameter expandable introducer sheath into a vessel to minimize puncture site trauma (primarily the size of the opening in an arterial wall). Then, if at a later time, a larger introducer sheath is required, the physician can manipulate the expandable introducer sheath to expand its inner diameter instead of having to exchange the smaller size sheath for a larger size sheath. This will lead to reduced patient healing times in at least two ways. First, physicians can initially use the smallest size introducer sheath suitable and, in many cases (where a larger sheath is not later required), this substantially minimizes the size of the arterial wall opening. Second, even if a larger inner diameter introducer sheath is later required, this alleviates the time-consuming and injurious conventional technique of removing the smaller sheath and then re-establishing a larger sheath within the vessel (at the same or a different puncture site).

BRIEF DESCRIPTION OF THE DRAWINGS

FIG. 4A illustrates another embodiment of the sheath of the present invention including a fold formed in a wall of the sheath and showing a mandrel prior to its insertion in the sheath.

FIG. 4B shows a sectional view as taken along lines 4B—4B in FIG. 4A.

FIG. 4C shows the folded sheath embodiment of the present invention with a mandrel inserted partially therethrough.

FIG. 4D illustrates a sectional view as taken along lines 4D—4D in FIG. 4C.

FIG. 4E illustrates a sectional view as taken along lines 4E—4E in FIG. 4C.

FIG. 4F illustrates a sectional view taken along lines 4F—4F in FIG. 4C.

FIG. 4G illustrates the folded sheath embodiment in its expanded size after insertion and removal of the mandrel.

FIG. 5A illustrates another embodiment of the present invention including an outer sheath coaxially disposed on an inner sheath and remaining outside the skin surface.

FIG. 5B shows an enlarged sectional view of a portion of the inner sheath and the outer sheath.

FIG. 5C shows the outer sheath disposed within the vessel and the inner sheath removed from within the vessel.

FIG. 5D shows an intravascular device 170 extending through the outer sheath disposed within the vessel.

Figure 1A:
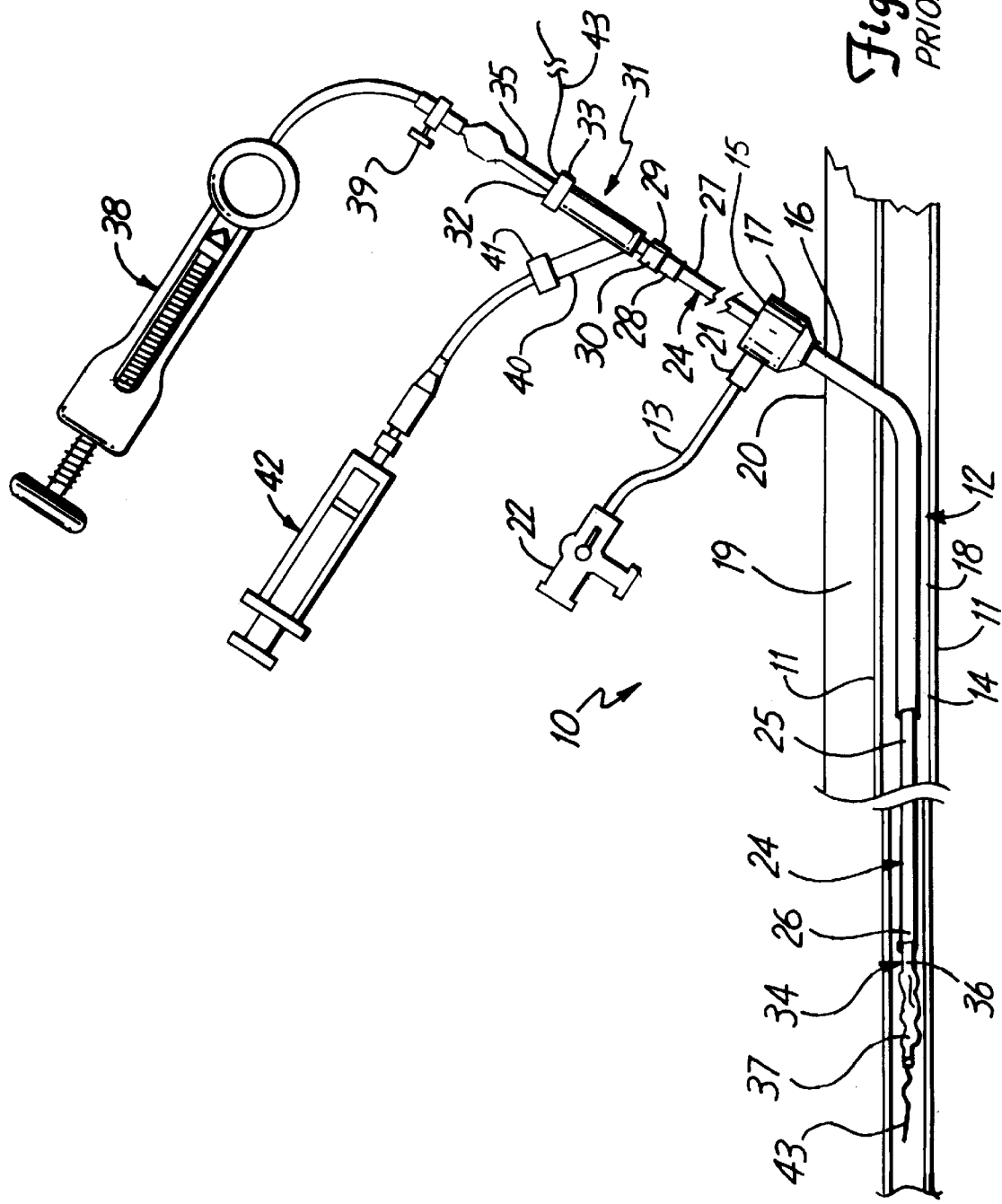
FIG. 1A illustrates an angioplasty dilatation catheter system including a guide catheter, dilatation catheter, and guide wire operatively disposed within an introducer sheath inserted percutaneously through the skin.

While the above identified drawing features set forth preferred embodiments, other embodiments of the present invention are also contemplated, as noted in the discussion. This disclosure presents illustrative embodiments of the present invention by way of representation and not limitation. Numerous other modifications and embodiments can be devised by those skilled in the art which fall within the scope and spirit of the principles of this invention. The figures have not been drawn to scale as it has been necessary to enlarge certain portions for clarity. For example, the change in the inner and outer diameters of the sheath tubing shown before (e.g., FIG. 2B) and after expansion (e.g., FIG. 2D) of the sheath has been exaggerated. In addition, a hub at a proximal end of the sheath also has been enlarged for clarity.

DETAILED DESCRIPTION OF THE PREFERRED EMBODIMENTS

The present invention comprises a method and apparatus for providing an expandable introducer sheath. The present invention allows a physician to initially choose a small size introducer sheath to minimize the size of the opening in the arterial wall (e.g., femoral artery) yet have the flexibility of having a larger size introducer sheath without the need to repeat a complete percutaneous insertion procedure (that must be performed when exchanging a conventional introducer sheath for a second larger introducer sheath). To fully understand the advantages of the present invention, it is necessary to review the percutaneous insertion procedure for placing an introducer sheath within a vessel, such as a femoral artery. This will highlight the complexity and disadvantages that arise if a percutaneous insertion procedure had to be repeated, and simultaneously provide insight into the advantages and benefits of providing an expandable introducer sheath of the present invention.

I. A Typical Percutaneous Insertion Procedure for Placing an Introducer Sheath within a Vessel An expandable introducer sheath of the present invention can be employed in many contexts for introducing intravascular and intralumenal devices within the human body. For example, the expandable introducer sheath of the present invention may be employed in an angioplasty catheter system as illustrated generally at 10 in FIG. 1A which is shown employing a conventional-type introducer sheath 12. The conventional (non-expandable) introducer sheath 12 of the catheter system 10 has a distal end 14 and a proximal end 16 with a tubular shaft 18 extending therebetween. A tubular entry port 17 extends proximally from the proximal end 16 of the sheath 12. The distal end 14 and a majority of shaft 18 of the sheath 12 are shown extending within the vessel 11. A remainder of the shaft 18 and the proximal end 16 of the sheath 12 are shown extending proximally outward from a wall of the vessel 11 through the skin tissue 19 and puncture site 20. A side port 21 of the sheath 12 extends laterally from the port 17 and provides a connection for fluid communication with a flexible tube 13 having a three-arm connector 22 for connecting desired devices to control blood flow (e.g. perfusion) or drug infusion within the vessel. The port 17 also includes a hemostasis valve 15 carried therein (see FIG. 1D) which provides a fluid-tight seal about intravascular devices (or other devices) passing through the proximal end of the port 17.

A guide catheter 24 of the catheter system 10 has a flexible shaft 25 which extends through the introducer sheath 12 and has a distal end 26 extending distally beyond the distal end 14 of the sheath 12 into the vessel 11. A proximal end 27 of the guide catheter 24 extends proximally outward outside of the patient's body beyond the port 17 of the sheath 12. A threaded luer lock fitting 29 releasably secures the proximal end 27 of the guide catheter 24 to a distal end 30 of a Y-adaptor manifold 31. A proximal end 32 of the Y-adaptor manifold 31 includes a Touhy-Borst compression seal 33 which forms a fluid-tight seal around a shaft of an angioplasty dilatation balloon catheter 34 (shown extending through the guide catheter 24).

The dilatation catheter 34 of the catheter system 10 has a proximal end 35 and a distal end 36 with a balloon 37 formed thereon. The balloon 37 is inflatable by an inflation device 38 connected to the proximal end 35 of catheter 34 by way of a three-way valve fitting 39. The Y-adaptor 31 further includes a side port 40 having a Touhy-Borst compression seal 41. The side port 40 is adapted to receive a syringe 42 (via a manifold) containing a radiopaque dye which is injected through the guide catheter 24 (via Y-adaptor 31) to the coronary arteries in a conventional manner. A guide wire 43 extends through a distal portion of the dilatation catheter 34 and, in the case of a single operator angioplasty catheter, the guide wire 43 extends alongside the dilatation catheter through a majority of guide catheter 24 until exiting at the proximal end 32 of the Y-adaptor 31.

The introducer sheath 12 provides a pathway through the skin tissue 19 (i.e. surface of the skin and the underlying tissue adjacent the vessel) into the vessel 11 to facilitate passage of the guide catheter 24, the balloon catheter 34 and the guide wire 43 in and out of the vessel 11 as desired. Typically, the introducer sheath 12 is positioned within the vessel 11 through the skin tissue 19 prior to the insertion of any intravascular device. For example, the sheath 12 may be placed in the vessel 11 through a percutaneous insertion method such as the following technique. A thin walled hollow puncture needle 44, as seen in FIG. 1B, is inserted through the skin tissue 19 so that a distal end of the needle 44 passes through a wall of the vessel 11 and extends into a lumen defined by the vessel 11. Next, a distal end of a thin metal guide wire 46 is inserted into a proximal end of the needle 44 and is threaded therethrough until a distal end of the wire 46 extends into the vessel 11 distally beyond the distal end of the needle 44, while a proximal end of the wire 46 extends proximally outward from a proximal end of the needle 44 as seen in FIG. 1B. While maintaining the wire 46 in place within vessel 11 (by grasping a proximal end of the wire 46), the needle 44 is withdrawn proximally over the wire 46 and out of the vessel 11 and the skin tissue 19 until only the wire 46 remains in the vessel 11.

Next, the sheath 12 must be prepared for insertion into the vessel 11. A dilator 48 (an elongate flexible cylinder having a bore extending therethrough) is inserted into the proximal end 16 of the sheath 12. The dilator 48 is advanced distally therethrough until a distal portion of the dilator 48 extends beyond the distal end 14 of the sheath 12 and a proximal portion of the dilator 48 releasably locks (by friction fit and the like) with and extends outward from the proximal end 16 of the sheath 12. The sheath 12 and dilator 48 now comprise an assembled unit for insertion into the vessel 11.

Figure 1B:
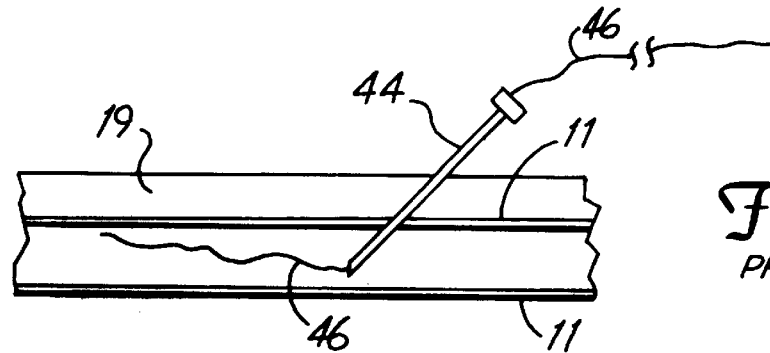
FIG. 1B illustrates a puncture needle and guide wire extending therethrough extending into a vessel through the skin.
Figure 1C:
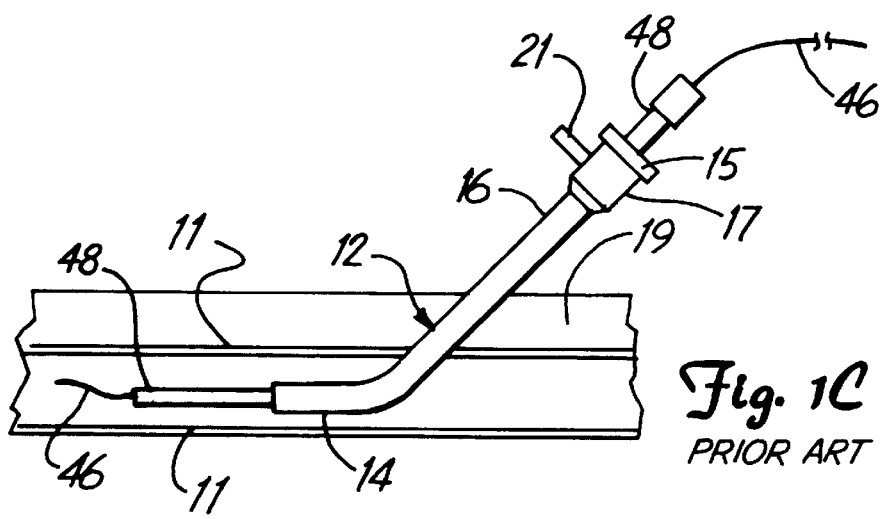
FIG. 1C illustrates an introducer sheath threaded over a dilator with both extending into the vessel.

To insert the sheath 12 in the vessel, the dilator 48 (with the sheath 12 loaded thereon) is advanced distally over the wire 46 until the distal portion of both the dilator 48 and sheath 12 extend into the vessel 11 and a proximal end of both the dilator 48 and sheath 12 extend proximally outward through the skin tissue 19 as shown in FIG. 1C. The tapered distal portion of the dilator 48 gradually dilates or expands the pathway through the skin tissue 19 and the opening in the wall of vessel 11 to accomodate the larger outer diameter of the sheath 12. The dilator 48 also provides rigidity to the thin walled sheath 12 during insertion into the vessel.

Figure 1D:
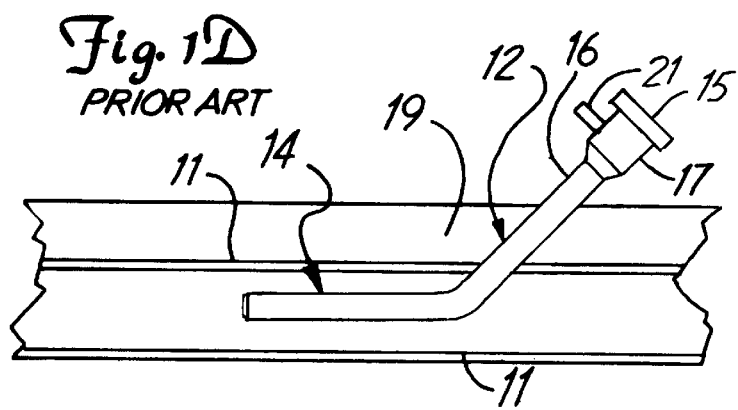
FIG. 1D illustrates the introducer sheath extending into the vessel through the skin.

The sheath 12 (still loaded onto and locked to the dilator 48) is advanced into the vessel 11 until the port 17 of sheath 12 is proximally adjacent the skin puncture site 20 (like that shown in FIGS. 1A and 1D). Next, while maintaining the position of the sheath 12 in the vessel 11, the sheath 12 is unlocked from the dilator 48 and the wire 46 and dilator 48 are withdrawn proximally through the proximal end 16 of the sheath 12 until only the sheath 12 remains within the vessel 11 as shown in FIG. 1D. At this point, the sheath 12 is ready to slidably receive the desired intravascular devices. Typically, the next step involves threading the guide catheter 24 through the sheath 12 and advancing and positioning the guide catheter 24 within the cardiovascular system. After positioning the guide catheter 24, other intravascular components are maneuvered through the guide catheter 24 until the configuration shown in FIG. 1A has been achieved. Although FIG. 1A illustrates a single operator exchange catheter system, other systems such as an over-the-wire or fixed wire dilatation catheter system may be used with an introducer sheath.

Although this is a common technique applied for percutaneously inserting an introducer sheath for introducing intravascular devices, other techniques may be employed. In any case, after placing the sheath 12 in the vessel 11 in this manner, the desired diagnostic or therapeutic procedure may be performed, including an angioplasty procedure using the desired intravascular treatment. For example, an angiography procedure (which does not use a guide catheter) could be performed for viewing (via fluoroscopy) the coronary arteries to observe the blood flow in that region.

An angiography typically is performed with a relatively smaller size catheter, such as a 5, 6, or 7 French size catheter. A "French" is a unit of measurement which roughly corresponds to one-third of a millimeter (or 0.013 inches), and is used to designate the diameter of the catheter or other lumenal intravascular device. Accordingly, a size 6 French catheter would have diameter of about 0.078 inches.

Prior to inserting an angiography catheter into a vessel, an introducer sheath is typically positioned within a vessel and protrudes out of the patient's body in the manner previously described. The introducer sheath typically is selected to have an inner diameter slightly greater than the outer diameter of the angiographic catheter. An angiography procedure may begin by threading a distal end of an angiography catheter into the proximal port 17 of sheath 12 and advancing the catheter distally therethrough into the vessel and through the cardiovascular system until its distal end is adjacent the coronary arteries. The proximal end of the angiographic catheter extends proximally outward through the sheath port 17 outside of the patient's body. After using the angiographic catheter to observe the coronary vasculature (or other system), the angiography catheter is then removed from the cardiovascular system by withdrawing it proximally out of the sheath 12 through port 17.

At this point, one may terminate the surgical procedure. However, an angioplasty procedure may follow the angiography procedure. An angioplasty procedure using the angioplasty catheter system 10 as described would have a guide catheter as its largest device (in diameter) to pass through the introducer sheath 12. The guide catheter typically has a size 7, 8, or larger French diameter that is larger than the size introducer sheath used for the angiography catheter that would still be in position within the vessel 11. Accordingly, the smaller size introducer sheath used for the angiographic procedure would have to be replaced with a larger size introducer sheath to accommodate the larger size guide catheter.

To do so, the sheath 12 must be withdrawn proximally out of the vessel 11 and skin tissue 19. This includes removing some sutures typically used to hold or anchor the proximal end of the sheath in place at the puncture site 20.

In the case where the original puncture site is to be re-used, the introducer sheath 12 is removed in the following manner. First, with the sheath 12 still in place within the vessel, the dilator 48 is re-inserted into the sheath 12 and advanced distally therethrough until both the sheath 12 and dilator 48 are once again locked together. Next, the wire 46 is threaded through the dilator 48 until extending within the vessel 11 distally beyond the dilator 48 and sheath 12. While maintaining the wire 46 within the vessel 11, the dilator 48 and sheath 12 are removed from the vessel 11 until both are outside the patient's body.

To introduce a new larger introducer sheath, the larger sheath is loaded onto a dilator and both the dilator and sheath are threaded over the wire in place within the vessel 11. The sheath is then positioned within the vessel 11 as previously described and the dilator and wire are removed from within the vessel.

If a second puncture site along the vessel wall is used, then the entire percutaneous insertion method previously described for inserting introducer sheath 12 would have to be performed again for the larger size introducer sheath at the new puncture site. This includes the following steps: inserting the puncture needle 44 through skin 19 into the vessel 11; threading the wire 46 through the needle 44 (FIG. 1B); removing the needle 44 from the vessel 11 while maintaining the wire 46 within the vessel 11; threading the dilator 48 and sheath 12 over the wire 46 and into the vessel 11 (FIG. 1C); and removing the dilator 48 and wire 46 from the sheath 12 resulting in the configuration of FIG. 1D.

Performing this second percutaneous insertion procedure wastes time, wastes an additional introducer sheath (and associated wire, needle, dilator), and creates extra bleeding. Moreover, this also creates another opportunity for bacterial infection, undesired thrombogenic activity and potential loss of a blood volume. More importantly, in the case of re-using a puncture site in the vessel wall, inserting a larger introducer sheath (in exchange for a smaller one) re-traumatizes the opening in the wall of the vessel through which the sheath extends. This results in longer clotting times to close the opening at the end of the surgical procedure and longer recuperation times to ensure stability in the healed puncture site in the arterial/vessel wall. In the case of using a second puncture site along the vessel, longer clotting and recuperation times are required because two openings must be closed and stabilized.

Faced with the disadvantages of exchanging introducer sheaths, physicians typically choose an introducer sheath that is larger than necessary to avoid the possibility of having to perform a sheath exchange. Although less traumatic than an exchange, creating a larger than necessary opening in the arterial wall undesirably increases the time required for clotting and long-term recuperation after the surgical procedure. This, in part, may result in a costly overnight stay in a hospital. It is highly desirable to reduce these times when possible either by not performing conventional introducer sheath exchanges, or by using the smallest size introducer sheath whenever possible. Reducing these times may allow such procedures to be performed regularly on an outpatient basis thereby significantly reducing the overall cost of the surgical procedure.

II. Providing an Expanded Inner Diameter Introducer Sheath

A. A First Expandable Introducer Sheath of the Present Invention

Figure 2A:
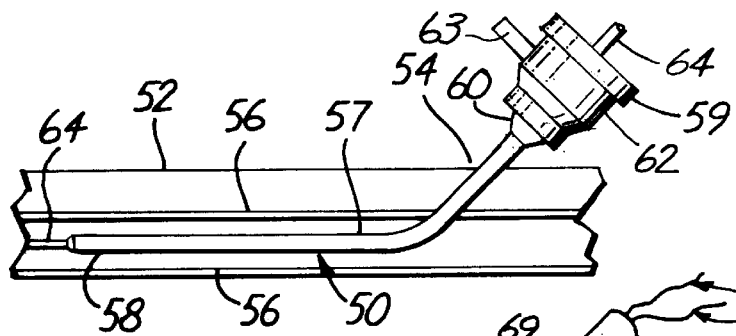
FIG. 2A illustrates an expandable introducer sheath of the present invention with an intravascular device extending proximally outward therefrom.

As seen in FIG. 2A, a first expandable introducer sheath 50 of the present invention is shown coaxially disposed within a vessel 56 below a surface of skin tissue 52. The sheath 50 includes an elongate flexible tubular shaft 57 extending between a distal end 58 and a proximal end 60. A hub 62 is preferably attached to the proximal end 60 of the sheath via a strain relief member 61 (FIG. 2B) by means of injection molding the hub 62 about the sheath proximal end 60 and strain relief member 61. The hub 62 includes a hemostasis valve 59. A side port 63 extends from the hub 62 for connecting with a flexible tube having a 3 way connector (not shown) for interfacing with blood flow management (perfusion) or drug infusion devices to be in fluid communication with the first sheath 50. The shaft 57 of the first sheath 50 is made of a shape-memory polymer material such as a polyurethane material having a tightly controlled glass transition temperature (e.g., 45° C.) that is slightly above normal human body temperature.

To employ the first expandable introducer sheath 50 of the present invention, the first introducer sheath 50 is initially inserted into the vessel 56 through skin tissue 52 by the method of percutaneous insertion previously described for inserting conventional introducer sheaths within a vessel (see FIGS. 1A–1D and accompanying discussion). Inserting the first introducer sheath 50 in this manner results in the configuration shown in FIG. 2A in which a distal portion of the shaft 57 of the first introducer sheath 50 extends coaxially through the vessel 56 while a proximal portion of the shaft 57 of the first introducer sheath 50 protrudes proximally outward from the surface of skin tissue 52. An intravascular device 64, such as a guide catheter inserted into the first introducer sheath 50, extends through the first introducer sheath 50 and distally beyond the distal end 58 of the first introducer sheath 50 to extend through the cardiovascular system to a region adjacent the coronary arteries. A proximal end of the intravascular device 64 protrudes proximally out the proximal end 60 of the first introducer sheath 50.

Frequently, it is determined that the intravascular device 64 must be exchanged for another, larger intravascular device. In conventional introducer sheath systems, the first introducer sheath would have to be removed and replaced by the larger introducer sheath with a repetition of the entire percutaneous insertion procedure (FIGS. 1A–1D discussion). However, in the case of the first introducer sheath 50 of the present invention, the first introducer sheath 50 can be manipulated to have a larger inner diameter size sufficient to accommodate the larger second intravascular device without removing the first introducer sheath 50 from its position within the vessel. To do so, however, any intravascular device 64 (with the exception of an unobtrusive wire such as coronary guide wire) must be removed from the first introducer sheath 50.

Figure 2B:
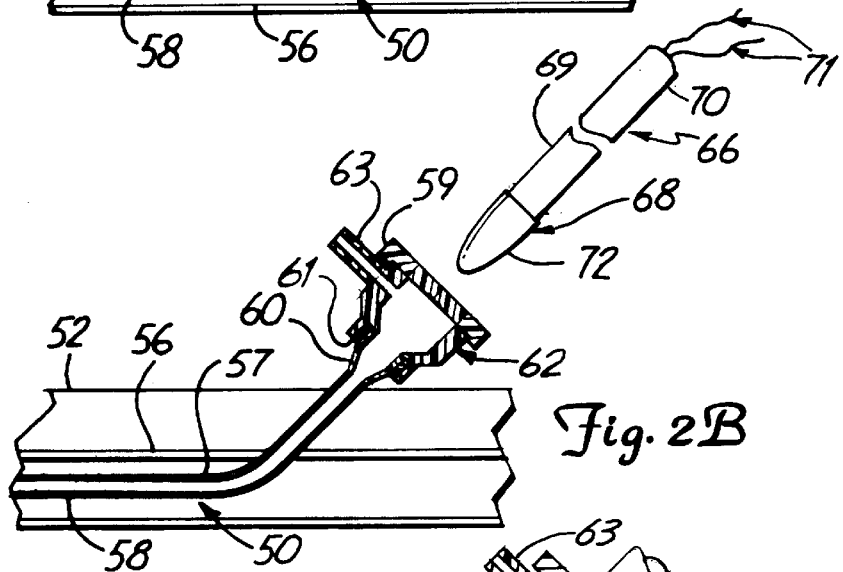
FIG. 2B illustrates the sheath of the present invention with a mandrel adjacent thereto prior to insertion of the mandrel.

As seen in FIG. 2B, a mandrel 66 is provided to facilitate employing the inventive first introducer sheath 50. The mandrel 66 is an elongate generally flexible rod having a distal portion 68 and a proximal end 70 with a shaft 69 extending therebetween. The distal portion 68 has a rounded conical shape and has a predetermined outer diameter which is substantially equal to a predetermined outer diameter of the shaft 69. The distal portion 68 has a metallic surface (or other heat conductive material) and a heating element 72 carried therein which is capable of creating temperatures substantially in excess of the human body temperature (e.g., 20° C. greater than 37° C.).

Figure 2C:
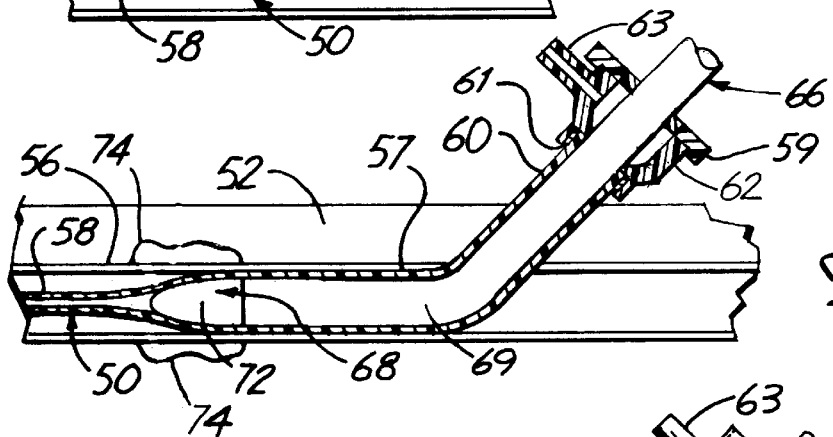
FIG. 2C illustrates the mandrel as inserted within the introducer sheath of the present invention.

To manipulate the first introducer sheath 50 to have an expanded inner diameter, the heating element 72 of the mandrel 66 is first activated, and then the distal portion 68 of the mandrel 66 is inserted into the proximal end 60 of the first introducer sheath 50 (through the hub 62) and pushed distally through the sheath 50 as shown in FIG. 2C. With the heating element 72 activated, the mandrel distal portion 68 heats the wall of the first introducer sheath 50 causing the shape-memory polymer material of sheath 50 to soften. This permits the mandrel distal portion 68 to forcibly expand the walls to form an inner diameter of the first introducer sheath 50 equal to an outer diameter of the mandrel distal portion 68 (and shaft 69).

Heating the first introducer sheath 50 in a region 74 adjacent the mandrel heating element 72, as seen in FIG. 2C, causes the shape-memory polymer material of the first introducer sheath 50 to exceed the glass transition temperature of the polymer material so that the material is easily stretched. When the polymer material is cooled below the glass transition temperature, the material will retain whatever shape the material is in at the time the material is cooled. Thus, for example, as seen in FIG. 2C, when the mandrel shaft 69 extends through the proximal portion of the first introducer sheath 50, the proximal portions of the sheath which have already cooled will retain an expanded inner diameter size equal to the outer diameter of mandrel shaft 69.

Segments of the sheath polymer material proximal to the heated mandrel distal portion 68 are cooled below the glass transition temperature (45° C.) by the surrounding body tissue and blood flowing about the first introducer sheath 50. The blood flowing around the first introducer sheath 50 creates a effective heat transfer mechanism and acts to quickly dissipate any heat stored in the first introducer sheath 50 as a result of the heated mandrel 66. Moreover, the first introducer sheath 50 typically is relatively thin (e.g. wall thickness of 0.006–0.011 inches) and therefore the first introducer sheath 50 is not readily capable of storing any substantial quantity of heat. This accentuates the transfer of heat from the shape memory polymer material to the blood and surrounding tissue. Thus, the sheath polymer material is cooled back to near human body temperature (e.g. 37° C.) well below the glass transition temperature (e.g. 45° C.) almost as soon as the heated distal portion 68 of mandrel 66 moves beyond a region of the sheath that has been heated and forcibly expanded. The expanded inner diameter of the sheath will be retained unless the shape-memory polymer of the first introducer sheath 50 is once again reheated above its glass transition temperature, and the first introducer sheath 50 reshaped.

The mandrel 66 is pushed distally through the first introducer sheath 50 expanding the inner diameter of the first introducer sheath 50 along its entire length until the distal portion 68 is beyond the distal end 58 of the first introducer sheath 50. After pushing the mandrel 66 through the entire length of the first introducer sheath 50, the heating element 72 is deactivated and allowed to cool below the glass transition temperature of the shape-memory polymer material. The mandrel 66 is then grasped at its proximal end 70 and withdrawn proximally outward through the hub 62 of the first introducer sheath 50 until the mandrel 66 no longer remains within the first introducer sheath 50. The resulting configuration of the expanded inner diameter first introducer sheath 50 is illustrated in FIG. 2D.

Figure 2D:
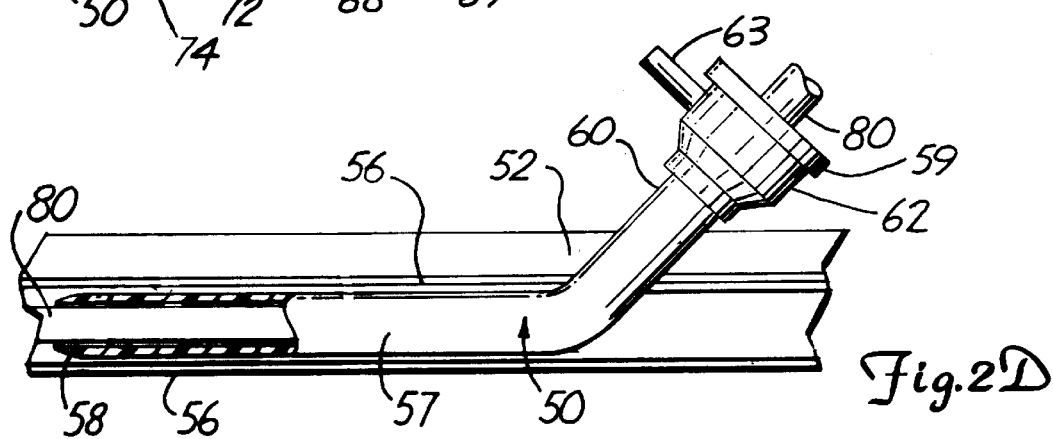
FIG. 2D illustrates an expanded size of the introducer sheath of the present invention after complete insertion and removal of the mandrel.

By comparing the inner diameter of the first introducer sheath 50 in FIG. 2D with the inner diameter of the first introducer sheath 50 in FIG. 2B, one can observe the relative increase (schematically depicted) in the inner diameter of the first introducer sheath 50. The relative increase in the inner diameter of the sheath 50 is not actually this dramatic but has been exaggerated in the drawings for illustrative purposes. Realistically, the inner diameter of the first introducer sheath 50 would be expanded 1 to 3 French sizes, i.e. about 0.013 to 0.039 inches. In addition, upon radial expansion of the sheath tubing, little change in wall thickness or length occurs. For example, the wall thickness of the first introducer sheath may be about 0.009 inches before radial expansion and about 0.008 inches after radial expansion. Similarly, a typical length for the first introducer sheath would be about 4 inches and this length would be about 3.8 inches after radial expansion.

To expand the inner diameter of the first introducer sheath 50 of the shape-memory material to desired French size (within a suitable range), one merely selects the outer diameter of the mandrel distal portion 68 (and shaft 69) to correspond to the desired inner diameter of first introducer sheath 50. For example, a size 6 French sheath can be readily expanded to a size 7 or 8 French size without substantially shortening the length of the sheath or adversely effecting the integrity of the polymer material.

Once the first introducer sheath 50 has been expanded to the desired inner diameter, a second intravascular device 80 having a outer diameter larger than the first intravascular device 64 can be inserted through the first introducer sheath 50 in the manner previously described for intravascular device 64. FIG. 2D shows the second intravascular device 80 as disposed within the expanded first introducer sheath 50.

The shape-memory material construction of the first introducer sheath 50 allows the sheath to be expanded by some number of French sizes while in place within the vessel 56. This allows the routine use of the smallest size sheath possible while still accommodating all necessary intravascular devices. For example, in a case where a smaller size sheath proved to be inadequate to accommodate all necessary intravascular devices, the sheath in place would be expanded. This creates, at most, the trauma that would have been required if that larger size sheath had been introduced originally but does not create the substantial additional trauma resulting from the conventional exchange of a smaller sheath for a larger one. Moreover, much time and effort is saved because the somewhat tedious multi-step percutaneous insertion method for an introducer sheath need not be performed again. Instead, a quick and simple insertion of the heated mandrel 66 expands the first introducer sheath 50 to the desired inner diameter sizing. Equally important, in a case where the smaller size introducer sheath proved to be sufficient to accommodate all necessary intravascular devices, the patient has been saved from having a larger than necessary opening in the vessel wall (e.g., femoral artery wall) as frequently happens when physicians initially choose a larger size introducer sheath.

Moreover, although the first expandable introducer sheath 50 has been described as being manipulated (expanded) with no intravascular devices extending through the sheath 50, a coronary guide wire can remain within the sheath 50 while the sheath 50 is being expanded by the heated mandrel 66.

The first introducer sheath 50 also can be expanded outside the patient's body (e.g. by means of the heated mandrel) before the sheath 50 is inserted into the vessel and before assembly with the dilator 48. This would permit a physician to stock a single size sheath on the shelf and create larger size sheaths only as needed. After being expanded, the sheath 50 would be cooled (while in its expanded size) by the ambient air (e.g. 25° C.) or by a liquid bath having a temperature (e.g. 25° C. or lower) well below the glass transition temperature of the shape memory polymer material of the first sheath 50.

The shape-memory polymer of the first introducer sheath 50 can be made from a suitable material having shape-memory characteristics, i.e., having a glassy state and a rubber state with a tightly controlled glass transition temperature defining the boundary therebetween. For example, the shape-memory polymer could be made of a ester-based polyurethane material having a high elasticity in the rubbery range and a glass transition temperature of about 45° C. This material is obtainable from the Mitsubishi Company and is sold as MM-4510 SMP resin. Alternatively, one can use an alloy polymer material comprising shape-memory material such as an ester-based polyurethane combined with an ordinary (non-shape-memory material) such as an ether-based polyurethane material (such as a material sold under the trade name Pellethane). The shape-memory polyurethane and ordinary polyurethane material can be mixed in a variety of compositions including a 50/50 composition having 50% shape-memory polyurethane and 50% ordinary polyurethane material. The composition can range from 50/50 up to a 90/10 composition of 90% shape-memory polyurethane to 10% of ordinary polyurethane material. In one combination, an ether-based polyurethane material (the shape-memory polymer) (#MM4520 from Mitsubishi Company) can be combined with an ester-based polyurethane material (Pellethane #2102 or 2355 BR available from the Dow Company of Midland, Mich.). The addition of the ordinary polyurethane material helps to prevent kinking of the first introducer sheath 50 while the sheath material is in the glassy state. The addition of the ordinary polyurethane material softens the sheath tubing more than using simply 100% polymer shape-memory polymer material and helps prevent the first introducer sheath 50 from shortening in length excessively upon being radially expanded by the heated mandrel. Of course, other polymeric materials which have shape-memory characteristics can be used and other alloying materials known to be combinable with such shape-memory polymers also can be used.

The first introducer sheath 50 can be formed by conventional extrusion techniques known to one skilled in the art. Although not discussed previously, the proximal end 60 of the sheath tubular shaft 57 preferably is pre-expanded (by heating) to have an inner diameter at least as large as the outer diameter of the mandrel shaft 69. This pre-expanded proximal end 60 of sheath shaft 57 is joined to an inner wall of a distal end of the hub 62 via strain relief member 61 as seen in FIGS. 2A and 2B. Alternatively, the proximal end 60 of sheath shaft 57 can be "over expanded" and then shrunk down about an outer wall of the distal end of the hub 62 and joined thereto via a strain relief member.

The portion of the mandrel 66 proximal to the distal portion 68 is a flexible tubular shaft made of a flouropolymer (e.g., Teflon®), polyethylene, or similar material. A pair of wire leads 71 extend through the mandrel shaft 69 to connect the heating element 72 within the distal portion 68 to a power source (not shown) outside of the mandrel 66. The mandrel heating element 72 can be a wire resistance coil or other suitable means known in the art for producing temperatures in the surface of distal portion 68 of about 50° C. to 65° C. This temperature is sufficient to heat the sheath material over 45° C. yet minimize any possibility of harming the surrounding tissue. A higher temperature producing heating element can be used if a shape memory polymer having a higher glass transition temperature is employed in the first introducer sheath 50. The heating element 72 also should be capable of dissipating heat quickly once the heating element 72 is deactivated. Moreover, the heating element 72 should produce heat in a controllable localized area surrounding the heating element 72.

B. A Second Expandable Introducer Sheath of the Present Invention

A second introducer sheath 90 of the present invention is illustrated in FIGS. 3A–3D. The second introducer second introducer sheath 90 has a tubular flexible shaft 92 extending from a distal end 94 to a proximal end segment 96. A hub 98 is attached to the proximal end segment 96 of the second introducer sheath 90 by a strain relief member 100. The hub 98 includes a hemostasis valve 97 for sealing about devices passing through the hub 98. The hub 98 also includes a side port 99 for connecting to an optional side tubing and connector like that shown in FIG. 1A.

Figure 3A:
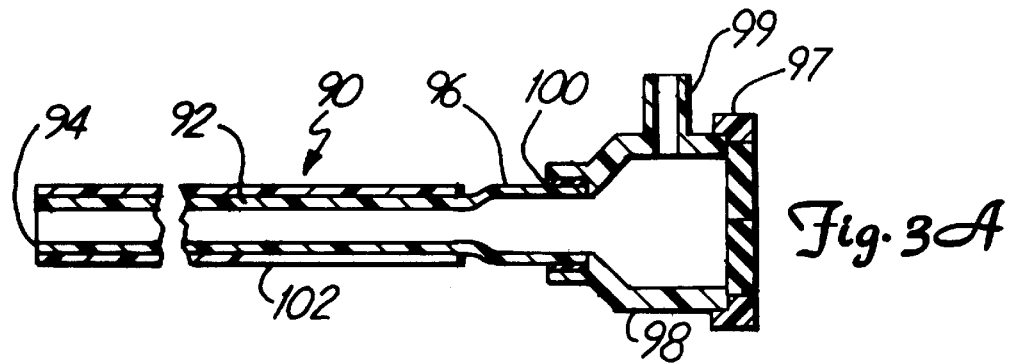
FIG. 3A illustrates another embodiment of the expandable introducer sheath of the present invention in cross-section.

The shaft 92 is made of a shape-memory polymer material such as polyurethane material with a tightly controlled glass transition temperature in the body temperature range and the material may include an additive such as an ordinary polyurethane material to comprise an alloy as previously described. The shaft 92 is extruded into its tubular shape having an initial inner diameter and an initial outer diameter equal to that shown for the proximal end segment 96 of the second introducer sheath 90 located proximally a protective sleeve 102. The hub 98 is joined to the proximal end segment 96 when in this initial diameter size by injection molding the hub 98 about the proximal end segment 96 and strain relief member 100. Then, by some method of force application (e.g., vacuum, linear stretching, mechanical compression, or the like) portions of the shaft 92 distally from the proximal end segment 96 are deformed to assume a smaller inner diameter such as shown in FIG. 3A. The inner diameter of the hub 98 is at least substantially equal to the inner diameter of the proximal end segment 96 of the second introducer sheath 90, which is the original inner diameter of the sheath shaft 92.

After "forming down" the sheath shaft 92, the protective sleeve 102 is slipped over the sheath shaft 92 to retain the shaft 92 in its reduced diameter state. The sleeve 102 is formed from a flouropolymer, polyethylene, or similar material. The sleeve 102 is generally inelastic radially at high temperatures above the glass transition temperature of the sheath material and is provided to prevent any inadvertent radial re-expansion of the sheath shaft 92 prior to the time such expansion is desired. The second introducer sheath 90 may be exposed to a variety of heat sources prior to insertion within the body that would cause re-expansion of the shape-memory polymer material comprising the sheath shaft 92 if not somehow constrained as by sleeve 102. For example, heat sources that may include heat during sterilization (e.g. above 100° C.), packaging, or shipping (e.g., up to 80° C.) could cause an unconstrained sheath shaft 92 to expand to its original inner diameter size because of the shape-memory characteristics of the polymer material.

Figure 3B:
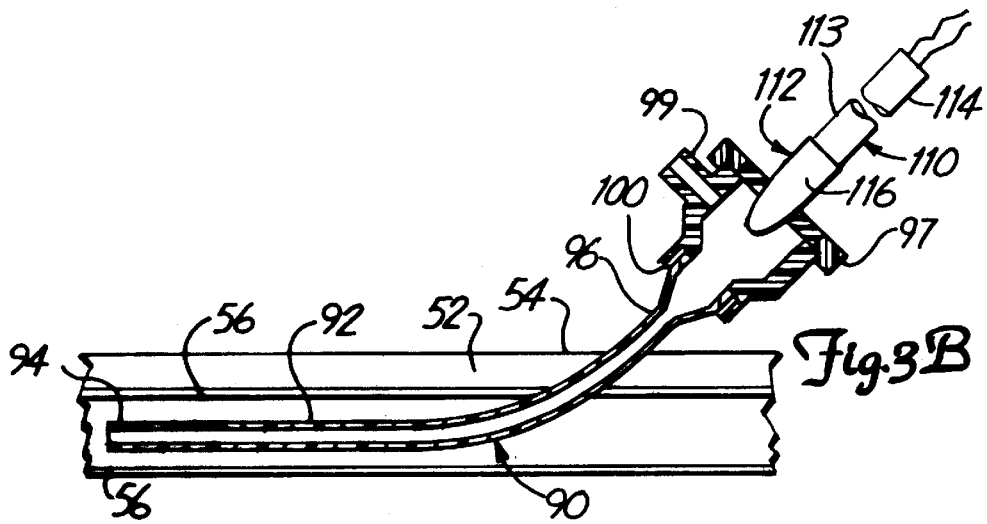
FIG. 3B illustrates the sheath of the present invention prior to insertion of a mandrel shown adjacent thereto the proximal end thereof.

To employ the second introducer sheath 90 of the present invention, the sleeve 102 is first removed from the second introducer sheath 90. The second introducer sheath 90 is then percutaneously inserted into the vessel 56 through skin tissue 52 in the manner described accompanying FIGS. 1A–1D. This results in the distal end 94 and the shaft 92 of the second introducer sheath 90 being disposed coaxially in the vessel 56 and the proximal end segment 96 of the second introducer sheath 90 (and hub 98) protruding proximally out of the surface of skin tissue 52, as shown in FIG. 3B. With the second introducer sheath 90 in this position, an intravascular device, such as an angiography catheter or a dilatation catheter, may be inserted. If it is determined that a larger intravascular catheter is required and that the second introducer sheath 90 has an inner diameter too small to accommodate the new intravascular device to be inserted, then a larger introducer sheath must be provided.

A mandrel 110 (similar to mandrel 66) as shown in FIG. 3B, is employed to manipulate the second introducer sheath 90 of the present invention to create a larger inner diameter for accommodating larger intravascular devices. The mandrel 110 has a distal portion 112 and a proximal end 114 with a heating element 116 disposed within the distal portion 112. The distal portion 112 is metallic and conducts heat produced by the heating element 116. A tubular polyurethane shaft 113 extends from the distal portion 112 to the proximal end 114 and carries a pair of leads connecting the heating element 116 to an outside power source (not shown). The shaft 113 may be made of a flouropolymer (e.g., Teflon®), polyethylene, or similar material. The heating element 116 is capable of being activated to reach temperatures of up to about 50° to 65° C.

Figure 3C:
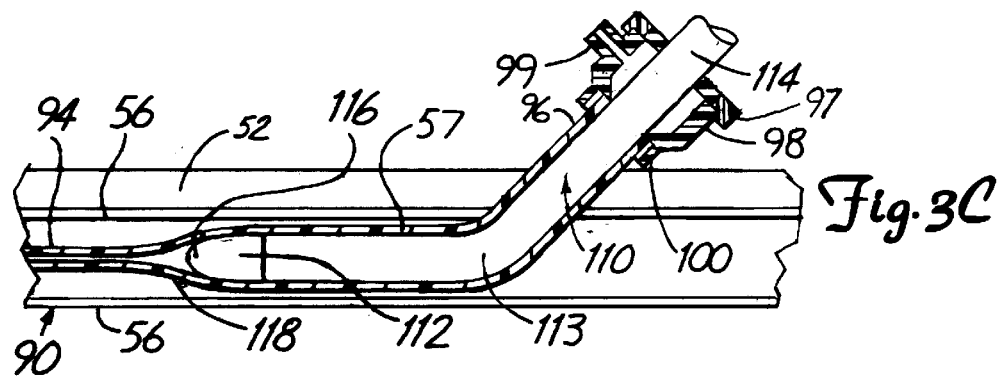
FIG. 3C illustrates the expandable introducer sheath with a mandrel extending partially therethrough.

Once the first smaller size intravascular device has been removed from the second introducer sheath 90, the manipulation of the sheath 90 to increase its size may begin. First, with the heating element 116 of the mandrel 110 activated, the distal portion 112 of the mandrel 110 is inserted into the proximal end 96 of the second introducer sheath 90 through the hub 98 and pushed distally through the second introducer sheath 90 as shown in FIG. 3C. The activated heating element 116 heats the walls of the second introducer sheath 90 above the glass transition temperature of the shape-memory polymer material causing the walls to soften. This permits the mandrel distal portion to forcibly expand the inner diameter of the second introducer sheath 90 to a size equal to the outer diameter of the mandrel distal portion 112 and shaft 113. As seen in FIG. 3C, the second introducer sheath 90 is heated in a region 118 adjacent the mandrel distal portion 112 and heating element 116 that causes the shape-memory material of the second introducer sheath 90 to exceed a glass transition temperature of the shape memory polymer material. Because the sheath of shape-memory material had been "shrunken down" from its original inner diameter size, the shape-memory material remembers its original shape which tends to help the forcible expansion caused by the heated mandrel 110.

Thus, with the heating element 116 activated, the mandrel 110 is pushed distally through the second introducer sheath 90, expanding the inner diameter of the second introducer sheath 90 along its entire length until the distal portion 112 is distally beyond the distal end 94 of the second introducer sheath 90. As the distal portion 112 (and activated heating element 116) of the mandrel 110 passes through the tubular second introducer sheath 90, portions of the sheath 90 proximal to the distal portion 112 will naturally cool below glass transition temperature of the shape-memory polymer material and "freeze" in an inner diameter equal to that of mandrel shaft 113. As shown in FIG. 3C, portions of the sheath proximal to the mandrel distal portion 112 have been expanded to a larger inner diameter. As in the embodiment of first introducer sheath 50, a coronary guide wire can remain within the second introducer sheath 90 during the expansion of the second introducer sheath 90 by the heated mandrel 110.

Figure 3D:
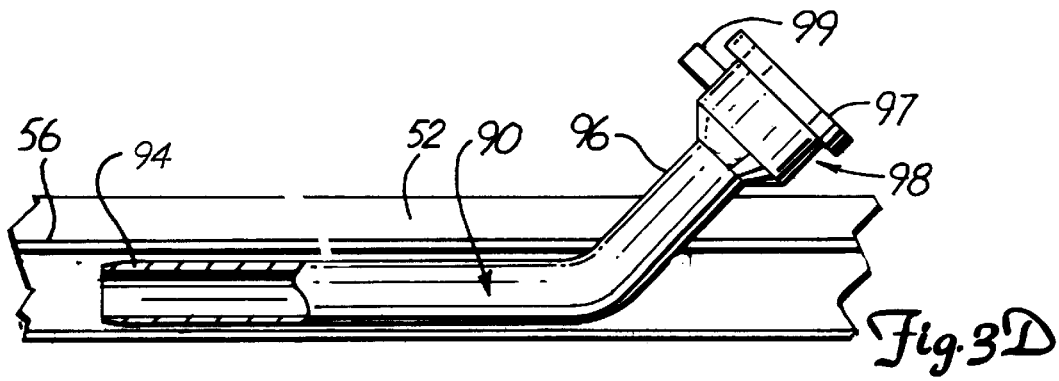
FIG. 3D illustrates the sheath of the present invention in its enlarged size after complete insertion and removal of the mandrel from the sheath.

After pushing the mandrel 110 through the entire length of the second introducer sheath 90, the heating element 116 is deactivated and allowed to cool. The mandrel 110 is then grasped at its proximal end 114 and withdrawn proximally outward through the sheath hub 98 until the mandrel 110 is completely removed from the second introducer sheath 90. The resulting configuration of the second introducer sheath 90 as expanded to its original inner diameter is illustrated in FIG. 3D. As in the illustration of the first introducer sheath 90, the relative increase in the inner diameter of the second introducer sheath 90 (after "snapping back" to original size) has been exaggerated for illustrative purposes. The relative increase in inner diameter typically would be about 2 French sizes.

Once the second introducer sheath 90 has been expanded to the original inner diameter size, the second intravascular device having an outer diameter larger than the first intravascular device can be inserted through the second introducer sheath 90 in the manner previously described. A typical length for the second introducer sheath 90 would be about 4 inches, although the length of the sheath in no way limits the advantages of the present invention. Similarly, the sheath 90 can have wall thickness of 0.006 inches up to 0.012 inches, and have diameters in the typical range of 5 to 11 French.

The second introducer sheath 90 preferably is constructed of the same polyurethane materials (or alloy thereof) as described for the first introducer sheath 50. Similarly, the second introducer sheath 90 preferably has a similar glass transition temperature (e.g. 45° C.) can be softened and expanded by means of the mandrel 110 capable of reaching temperatures of about 50°–65° C. in its distal portion 112. Of course, the mandrel 110 is of similar construction and performs like the mandrel 66 used with the first introducer sheath 50.

The first introducer sheath 90 made of the shape-memory polymer material also can be formed incorporating a tubular braided wire (or non-metallic material) matrix. This braided matrix would tend to expand radially along with and facilitate the expansion of the shape-memory polymer material. This results because the braided material matrix, like the shape-memory polymer, remembers its original size diameter (before being shrunken down) and when permitted, tends to return to the original size diameter. The tubular braided matrix also will tend to maintain the sheath 50 in a substantially uniform cylindrical or tubular shape during the radial expansion of the sheath 50.

The second introducer sheath 90 provides another way to provide an expanded inner diameter for an introducer sheath without having to remove the sheath from the vessel. This saves time and reduces trauma to the vessel wall opening and skin tissue, amongst other advantages of the present invention already discussed in the detailed description. Indeed, a unique feature of the second introducer sheath 90 results directly from the use of a shape memory polymer. Because of the characteristics of the shape-memory polymer material, as the second introducer sheath 90 is being expanded, the shape-memory polymer material "remembers" its larger original size inner diameter and accordingly, tends to facilitate the forcible expansion of the sheath by the heated mandrel.

C. A Third Expandable Introducer Sheath of the Present Invention

A third expandable introducer sheath 130 of the present invention is illustrated in FIGS. 4A–4G. The third introducer sheath 130 has a flexible tubular shaft 132 extending from a distal end 134 to a proximal end portion 136 of the third introducer sheath 130. A tubular hub 138 is attached to the proximal end portion 136 of the third introducer sheath 130 and has a hemostasis valve 139 carried thereon. The hub 138 is preferably injection molded about the proximal end portion 136 of the sheath 130. The third introducer sheath 130 has a longitudinal fold 140 extending along a substantial portion of the length of the shaft 132. As seen in FIG. 4B, the fold 140 is a portion of a wall 141 of the shaft 132 which has been folded over onto itself. The proximal end portion 136 of the sheath 130 tapers from the fold 140 to a larger diameter at a distal end of the hub 138. An adhesive 143 or other suitable means such as ultrasonic welding may be used to temporarily maintain the fold 140 against an outer surface of the wall 141 of the sheath 130. The third introducer sheath 130 is shown as coaxially disposed within the vessel 56 after insertion through a surface of skin tissue 52 by the percutaneous technique previously described in conjunction with FIGS. 1A–1E.

An angiographic, angioplasty or other diagnostic/therapeutic procedure can be performed through the third introducer sheath 130 as previously described for conventional introducer sheaths. If it is determined that an intravascular catheter is required having an outer diameter larger than the inner diameter of the folded shaft 132, then the third introducer sheath 130 of the present invention can provide an expanded inner diameter to accommodate the larger intravascular catheter without removal and exchange of the third introducer sheath 130. However, as in the first and second introducer sheaths (50 and 90), the third introducer sheath 130 provides the opportunity to use a smaller size opening in an arterial wall instead of necessarily using a larger size sheath (and a larger opening) to "play it safe" to avoid performing an exchange. Moreover, the third introducer sheath 130 of the present invention (as well as the sheath 50 and 90) also provide the opportunity to have a larger inner diameter sheath without performing a complete introducer sheath exchange and without removing the sheath 130 from within the vessel.

To expand the inner diameter of third introducer sheath 130, the first intravascular device (except a coronary guide wire or similarly unobtrusive intravascular device) must first be removed from the third introducer sheath 130 by proximally withdrawing the device therefrom. Next, a mandrel 142 is provided having a distal portion 144 and a proximal end 146. The distal portion 144 of the mandrel 142 is inserted into the hub 138 of the third introducer sheath 130 and pushed distally through the shaft 132 of the third introducer sheath 130 as seen in FIG. 4C. The distal portion 144 of the mandrel 142 has an outer diameter greater than the inner diameter of the sheath shaft 132 in its folded state (FIG. 4D). The mandrel 142 also may comprise a mandrel like one of those discussed in conjunction with the first or second introducer sheaths 50 and 90, respectively. The mandrel 142 may be made of any suitable generally flexible material, such as a polyethylene material, formed into a tubular configuration. Alternatively, instead of the mandrel 142, a guide catheter may be used to cause the fold 140 to unfold.

As the mandrel distal portion 144 is advanced distally through the shaft 132, the fold 140 is forced open. This breaks the adhesive seal or bond 143 on the wall 141 in a peeling fashion and allows the fold 140 to begin to unfold as seen in FIG. 4E. This corresponds to the folding transition region 145 in FIG. 4C. As seen in FIG. 4C, portions of the third introducer sheath 130 which are located proximally to the mandrel distal portion 144 are expanded to an extent that they no longer have a fold in the wall 141 of the sheath shaft 132. This configuration of the sheath shaft 132 is illustrated in FIG. 4F.

The mandrel distal portion 144 is pushed distally through the shaft 132 until it is passed through the entire length of the third introducer sheath 130 and exits the distal end 134 of the sheath. This causes the fold 140 to be forced open (i.e., unfolded) along the entire length of sheath shaft 132 so that the sheath shaft 132 assumes the cross section configuration shown in FIG. 4F. This is the expanded inner diameter size of third introducer sheath 130.

Next, the mandrel 142 is then withdrawn proximally through the third introducer sheath 130 and the hub 138 until the mandrel 142 no longer remains within the third introducer sheath 130. The third introducer sheath 130 in its expanded inner diameter configuration is shown in FIG. 4G. As seen in FIG. 4G, a second intravascular catheter 148 having a outer diameter larger than the first intravascular catheter is disposed within the third introducer sheath 130. In the case where a guide catheter was used (instead of the mandrel 142) to expand the third introducer sheath 130, the guide catheter would remain within the third introducer sheath 130 as the second intravascular device 148. Otherwise, the second intravascular device 148 would be introduced in the third introducer sheath 130 as previously described. The second intravascular device 148 typically would be about 2–3 French sizes larger than the previous intravascular catheter.

In addition, the third introducer sheath 130 may be made of any suitable tubing material including a shape-memory polymer. If a shape-memory polymer were used, then the third introducer sheath 130 could be expanded again beyond the size shown in FIG. 4G by employing a heated mandrel in a technique similar to that previously described for the first introducer sheath 50 of the present invention. However, a polyethylene material or other lubricous coating material (e.g. TEFLON® coated) is preferable. Alternatively, adhesion between the fold 140 and the wall 141 can be created by using ultrasonic welding techniques already known to those skilled in the art.

The third introducer sheath 130 of the present invention may produce a relative increase in inner diameter of about 2 to 4 French sizes. This corresponds to a change of about 0.026 to 0.052 inches. Of course, the drawings have been exaggerated for illustrative purposes and do not represent the appropriate relative change in inner diameter that occurs when employing the third introducer sheath 130 into its expanded inner diameter. The third introducer sheath 130 can be of conventional lengths of about 4 inches and even up to 12 inches. The third introducer sheath preferably has inner diameters in the folded position corresponding to 5 to 9 French sizes.

The third introducer sheath 130 shares the advantages of the other inventive introducer sheaths already discussed but the sheath can be employed (unfolded) with a mandrel (or expander) that does not have a heating element or with a guide catheter.

D. A Fourth Expandable Introducer Sheath of the Present Invention

As seen in FIGS. 5A–5D, a fourth expandable introducer sheath 151 of the present invention includes an assembly including a first inner sheath 150 and a second outer sheath 160. The inner sheath 150 has a shaft 152 extending between a distal end 154 and a proximal end 156. A hub 158 is attached to the proximal end 156 of the sheath 150 and has a hemostasis valve 159 carried therein. The outer sheath 160 has a shaft 162 extending between a distal end 164 and a proximal end 166. A hub 168 is attached at the proximal end 166 of sheath 160 and has a hemostasis valve 169 carried thereon. The outer sheath 160 is coaxially disposed about the sheath 150 as shown in FIGS. 5A and 5B. The outer diameter of the inner sheath shaft 152 is substantially equal to the inner diameter of the outer sheath shaft 162 and the inner sheath 150 is longer than the outer sheath 160. The inner sheath 150 may comprise a conventional introducer sheath having a length of about 10–12 inches and a 5, 6, or larger French size inner diameter. The outer sheath 160 also may comprise a conventional-type introducer sheath, except that it has a length of about 4 inches and an inner diameter that is one to two French sizes larger than the first sheath 150.

To employ the fourth expandable introducer sheath 151, the inner sheath 150 is percutaneously inserted in the manner previously described (in conjunction with FIGS. 1A–1E). In the resulting configuration, as seen in FIG. 5A, the inner sheath 150 has a distal portion of its shaft 152 extending through the vessel 56 while the distal end 164 of outer sheath 160 remains over a proximal portion of the shaft 152 of the inner sheath 150 (which remains outside the patient's body). An initial therapeutic or diagnostic procedure using an intravascular device would be performed with the sheath combination in the position shown in FIG. 5A. If it is discovered that an intravascular device having an outer diameter larger than the inner diameter of the sheath shaft 152 is required, then a larger inner diameter introducer sheath must be provided. The inner diameter of introducer sheath 151 can be effectively expanded by employing the inner and outer sheath combination without complete removal and reinsertion of introducer sheaths.

Whether or not the first smaller intravascular device has been removed from the sheath 150, the method of providing an expanded inner diameter introducer sheath can be initiated. First, the proximal end 156 of the inner sheath 150 is held generally stationary while the shaft 162 of the outer sheath 160 is distally advanced relative to and over the inner sheath shaft 152. The distal end 164 of the second outer sheath 160 thus enters the skin tissue 52 and vessel 56 guided by the first inner sheath 150. The distal end 164 of the outer sheath 160 is advanced distally through the vessel 56 until in the position shown in FIG. 5C, where the proximal end 166 of the outer sheath 160 is just proximally adjacent the surface of the skin tissue 52. After positioning the outer sheath 160 in this manner, the inner sheath 150 is withdrawn proximally outward from the outer sheath 160 while holding the outer sheath 160 generally stationary in its position within the vessel 56. The inner sheath 150 is fully withdrawn proximally from within the outer sheath 160 as shown in FIG. 5D. If the smaller intravascular device had not yet been removed from the inventive introducer assembly it must now be withdrawn in order to permit introduction of a second, larger device. The inner sheath 150 is then discarded and a second intravascular device 170 having an outer diameter larger than the inner diameter of inner sheath 150 is inserted into the outer sheath 160 to initiate an additional diagnostic/therapeutic procedure using the expanded introducer sheath.

The fourth introducer sheath 151 of the present invention advantageously employs conventional introducer sheath components to provide an expanded inner diameter sheath while maintaining an introducer sheath within the vessel. Moreover, as in the other embodiments of the present invention, the fourth introducer sheath 151 allows the physician to begin a procedure with a smaller size introducer sheath and not be wary of having to perform a "full-blown" introducer sheath exchange (the procedure described in discussion accompanying FIGS. 1A–1D).

The outer sheath 160 also can be expanded if necessary to accommodate even larger size intravascular devices. To do so, the second sheath 160 can be made of a shape-memory polymer material. This permits the outer sheath 160 to be manipulated in the manner described in association with FIGS. 2A–2E, using a heated mandrel to expand the inner diameter of the sheath 160. Alternatively, the outer sheath 160 could be formed in the manner described in association with FIGS. 3A–3E and manipulated with a heated mandrel to expand the inner diameter of the outer sheath 160. Indeed, even the embodiment of FIGS. 4A–4E could be employed in outer sheath 160 so that the inner diameter of outer sheath 160 could be expanded by pushing a mandrel through the outer sheath 160 to cause a fold in the wall of the outer sheath 160 to unfold yielding an expanded inner diameter outer sheath 160.

The use of the fourth expandable introducer sheath 151 (including the inner sheath 150 and the outer sheath 160) includes the insertion of the outer sheath 160 as a separate step from the insertion of the inner sheath 150. However, any additional trauma caused by this separate step in still much less than the trauma created by complete removal of a first sheath and then insertion of a second sheath requiring duplication of all the steps for percutaneous insertion. Moreover, the method using the fourth introducer sheath 151 saves much time and effort by avoiding a multi-step separate or repeated percutaneous insertion procedure for the second larger inner diameter sheath.

The inner sheath 150 and outer sheath 160 comprise conventional introducer sheaths made of conventional sheath materials such as polyethylene, ordinary polyurethane, polypropylene, and/or fluoropolymers. The inner sheath 150 typically has a length of about 10–12 inches so that the sheath 150 can extend within the vessel 56 while still having a sufficient length remaining outside the patient's body to carry the outer sheath 160 thereon until ready for use. The second outer sheath 160 is preferably one or two French sizes larger than the inner sheath 150. For example, the inner sheath 150 can have a size 6 French diameter suitable for angiographic catheters and the second outer sheath 160 can have a size 8 French diameter more suitable for accommodating angioplasty catheters. The first and second sheaths also have conventional wall thicknesses ranging from 0.006 inches to 0.011 inches.

E. A Fifth Expandable Introducer Sheath of the Present Invention

A fifth expandable introducer sheath 181 of the present invention, as illustrated in FIGS. 6A–6E includes an elongate inner sheath 180 having a flexible shaft 182 extending between a distal end 184 and a proximal end 186 with a hub 188 joined thereon at the proximal end 186. The hub 188 includes a hemostasis valve 189 carried therein. As before, the inner sheath 180 is inserted percutaneously in the manner previously described in conjunction with FIGS. 1A–1E so that the inner sheath 180 is disposed within the vessel 56 with a proximal end 186 of the inner sheath 180 protruding proximally out of the skin tissue 52.

If it is desired to insert an intravascular catheter having an outer diameter larger than that allowed by the inner diameter of the inner sheath 180, the fifth expandable introducer sheath 181 of the present invention can be manipulated to provide an expanded inner diameter sheath without requiring a complete removal of the sheath and percutaneous insertion of another introducer sheath (in the manner described with FIGS. 1A–1E). The method of expanding the inner diameter of the fifth introducer sheath 181 includes proximally withdrawing the shaft 182 of the inner sheath 180 outward from the vessel 56 and skin tissue 52 until in the position shown in FIG. 6B. In this position, a substantial distal portion of the shaft 182 of the inner sheath 180 remains within the vessel 56.

Next, a cylindrical rod 190 (which may have a bore extending therethrough to carry intravascular devices therethrough) is inserted into the proximal end 186 of the inner sheath 180 to obstruct the lumen of the shaft 182. This prevents backbleeding (i.e., blood flow) from the vessel 56 through the inner sheath 180 once the hemostasis valve 189 (and hub 188) is removed (as described later). The rod 190 provides rigidity and columnar support to the sheath shaft 182. After the rod 190 is firmly seated within the inner sheath 180, the inner sheath 180 is cut or manipulated so that the hub 188 of the inner sheath 180 is removed, either by cutting the hub 188 off at the shaft 182 or by providing an otherwise removable hub assembly. This can be accomplished by various means including a pre-formed transverse slit about the circumference of the shaft 182 adjacent the proximal end 186 of inner sheath 180 or by simply cutting through the shaft 182 with a blade designed to make the cut. These proximal portions of the inner sheath which are removed are illustrated in phantom in FIG. 6C.

Figure 6A:
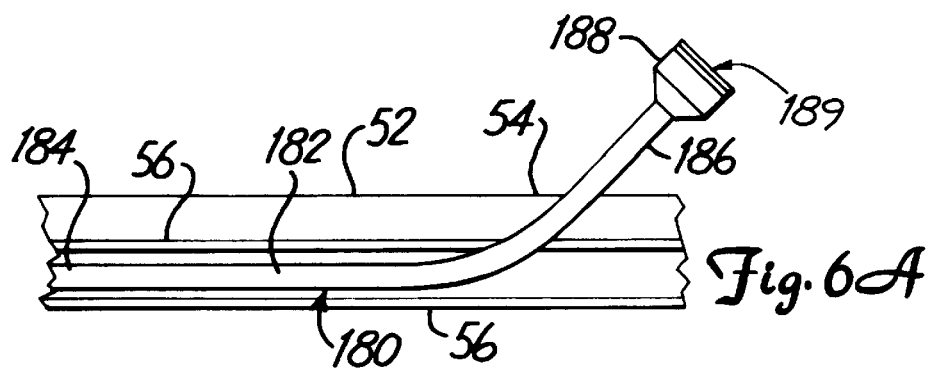
FIG. 6A illustrates an expandable introducer sheath of the present invention as disposed within a vessel percutaneously.
Figure 6B:
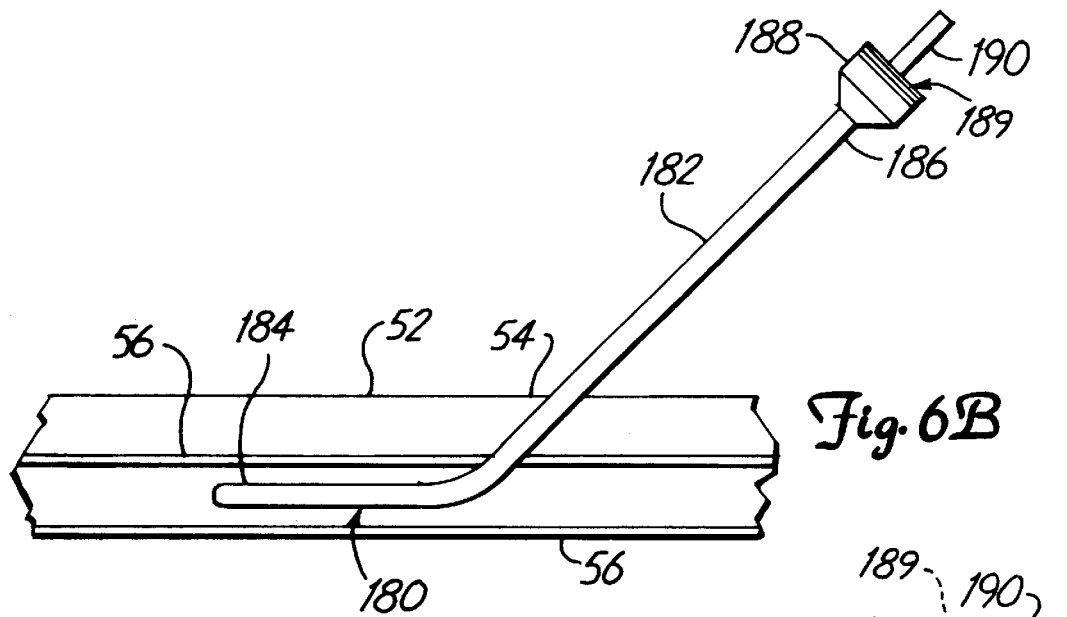
FIG. 6B illustrates a sheath of the present invention partially withdrawn from the vessel and having a rod extending outwardly therefrom.
Figure 6C:
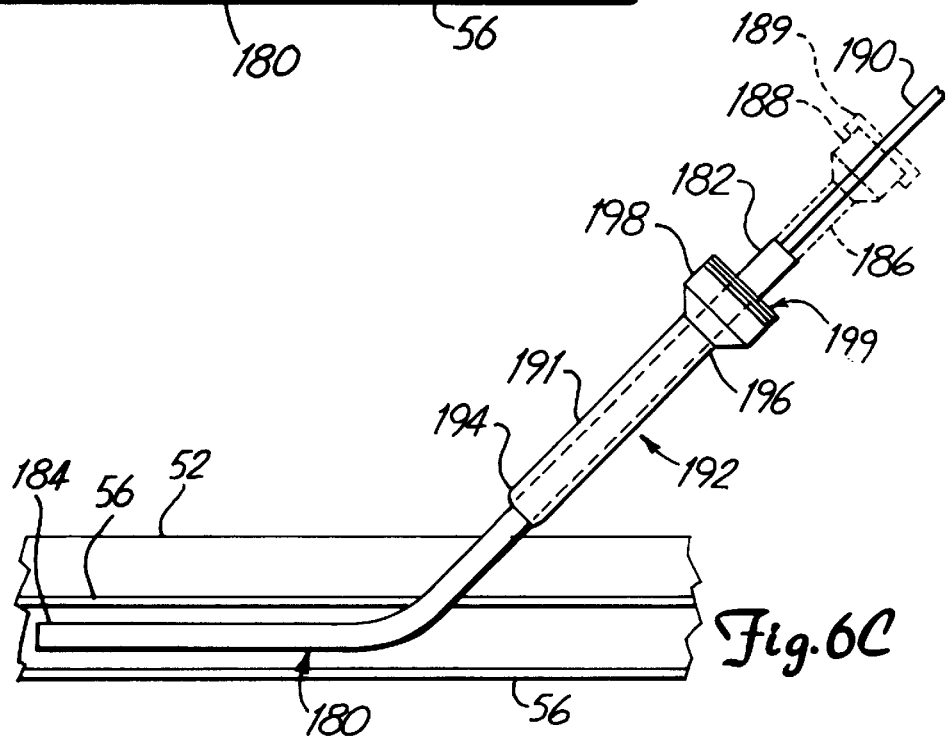
FIG. 6C illustrates a removed hub of the sheath in phantom and having a larger diameter outer sheath placed over the first sheath.
Figure 6D:
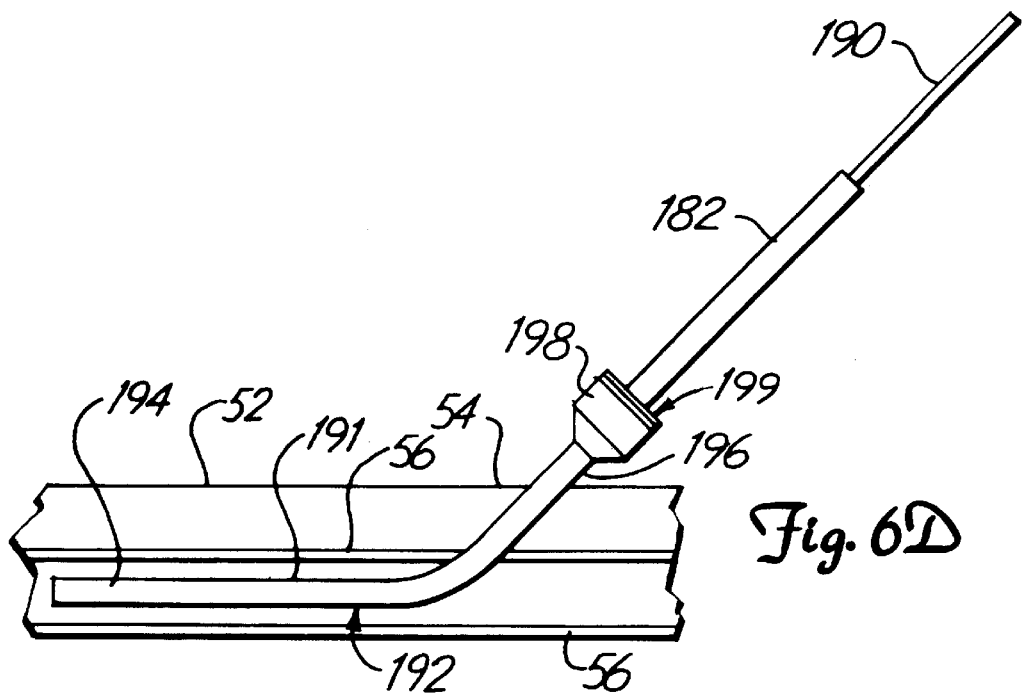
FIG. 6D illustrates the second sheath disposed percutaneously within the vessel and extending proximally outward through the skin surface with the inner long sheath and rod extending proximally outward therefrom.
Figure 6E:
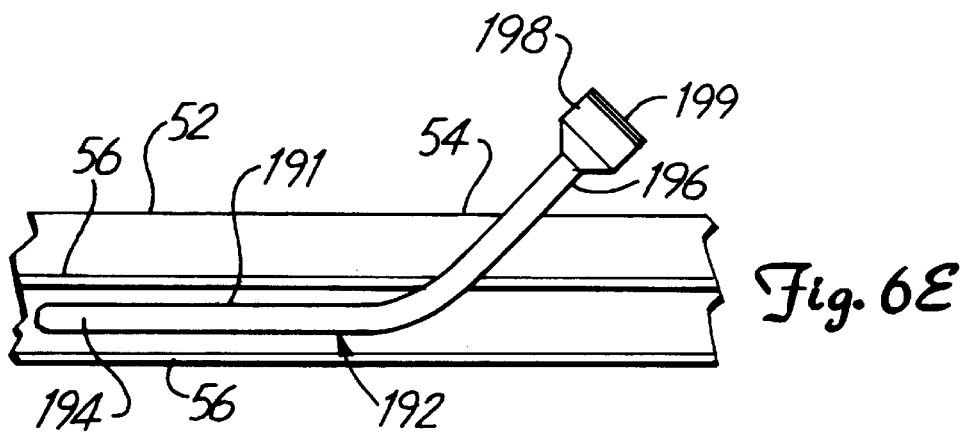
FIG. 6E illustrates the larger diameter sheath disposed within the vessel after removal of the longer inner sheath and rod.

Next, an outer sheath 192 is provided having a flexible elongate shaft 191 extending between a distal end 194 and a proximal end 196. The outer sheath 192 has a hub 198 similar to the hub 188 and has a hemostasis valve 199 carried therein. The outer sheath 192 also has an inner diameter equal to or larger than the outer diameter of the shaft 182 of the inner sheath 180. While holding a proximal end of the rod 190 or the inner sheath 180, the distal end 194 of the outer sheath 192 is advanced distally and coaxially over a proximal end of the rod 190 and the cut proximal end 186 of the inner sheath 180 until a distal end of the outer sheath 192 is just proximally adjacent the skin surface 52 as shown in FIG. 6C. While still holding the rod 190 and inner sheath 180 generally stationary, the outer sheath 192 is advanced distally through the skin tissue 52 and into the vessel 56, with the rod 190 and inner sheath 180 combination serving to guide the advancement of the outer sheath 192. The outer sheath 192 is advanced distally until its hub 198 is just proximally adjacent the skin surface 52 as shown in FIG. 6D. With the outer sheath 192 in place within the vessel 56, the rod 190 and inner sheath 180 are withdrawn proximally outward from the outer sheath 192 until only the outer sheath 192 remains within the vessel 56 as shown in FIG. 6E. At this point, an intravascular device may be inserted into the outer sheath 192 (of larger inner diameter) to perform another diagnostic or therapeutic procedure.

The outer sheath 192 also can be expanded if necessary to accommodate even larger size intravascular devices. To do so, the outer sheath 192 can be made of a shape-memory polymer material. This permits the outer sheath 192 to be manipulated in the manner described in association with FIGS. 2A–2E, using a heated mandrel to expand the inner diameter of the sheath 192. Alternatively, the sheath 192 could be formed in the manner described in association with FIGS. 3A–3E and manipulated with a heated mandrel to expand the inner diameter of the sheath 192. Indeed, even the embodiments of FIGS. 4A–4E could be employed in sheath 192 so that the inner diameter of sheath 192 could be expanded by pushing a mandrel through the sheath 192 to cause a fold in the wall of the sheath 192 to unfold yielding an expanded inner diameter second sheath 192.

The use of the fifth expandable introducer sheath 181 of the inventive embodiment illustrated in FIGS. 6A–6E includes the insertion of the outer sheath as a separate step from the insertion of the inner sheath. However, any additional trauma caused by this separate insertion step is still much less trauma than that created by complete removal of a first sheath and then insertion of a second sheath requiring duplication of all the steps for percutaneous insertion. Moreover, the sheath expansion method used provided by the sheath combination of inner sheath 180 and outer sheath 192 saves much time and effort by avoiding the multi-step percutaneous insertion procedure for a second sheath (in the manner described with FIGS. 1A–1E). More importantly, the fifth expandable introducer sheath 181 overcomes the much discussed physician's dilemma of wanting the smaller size introducer sheath yet choosing a larger then necessary size introducer sheath to avoid having to perform an introducer sheath exchange. The present invention allows a smaller size sheath to be used initially and still provide an expanded introducer sheath if necessary without having to perform a conventional introducer sheath exchange.

F. A Sixth Expandable Introducer Sheath of the Present Invention

Figure 7B:
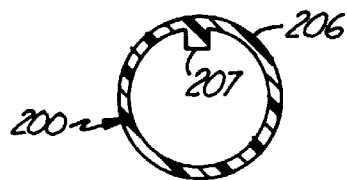
FIG. 7B illustrates an enlarged sectional view as taken along lines 7B—7B in FIG. 7A.
Figure 7C:
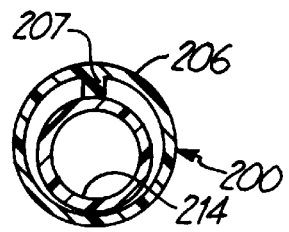
FIG. 7C illustrates a sectional view similar to FIG. 7B except showing a guide catheter disposed within the sheath.
Figure 7A:
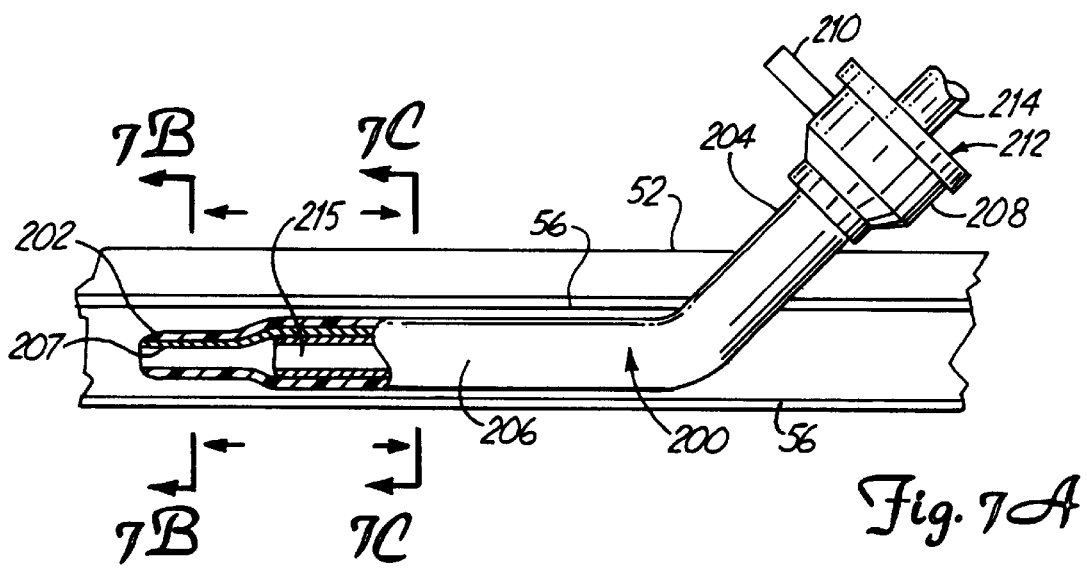
FIG. 7A illustrates an expandable introducer sheath of the present invention including a rib extending longitudnally on an inner wall of the sheath.

A sixth expandable introducer sheath 200 of the present invention, as illustrated in FIGS. 7A–7C includes an elongate flexible shaft 206 extending between a distal end 202 and a proximal end 204 with a hub 208 joined thereon at the proximal end 204. The hub 208 includes a hemostasis valve 212 carried therein and a connector outlet 210 extending from a side of the hub 208. As least one rib 207 extends longitudinally on an inner wall of the sheath shaft 206. This sheath 200 can be inserted percutaneously in a manner previously described in conjunction with FIGS. 1A–1E so that the sheath 200 is disposed within the vessel 56 with a proximal end 204 of the sheath 200 protruding proximally out of the skin tissue 52.

If it is desired to insert an intravascular catheter having an outer diameter larger than the inner diameter of the inner sheath 180, the sixth expandable introducer sheath 200 of the present invention allows for expansion of the inner diameter without requiring a complete removal of the sheath and percutaneous insertion of another introducer sheath (in the manner described with FIGS. 1A–1E).

The shaft 206 of the expandable introducer sheath 200 is made of an elastomeric tubing material such as a polyurethane, latex, Kraton®, silicone rubber or other elastomeric material that is both flexible and stretchable, i.e., capable of being radially expanded by mechanically applied pressure within the sheath shaft 206, such as by the insertion of a guide catheter. This capability is illustrated in FIG. 7A in which an intravascular device 214 such as a guide catheter is shown extending within the sheath shaft 206. Portions of the shaft 206 of the sheath 200 which are distal to a distal end 215 of the intravascular device 214 are shown having a diameter smaller than portions of the sheath shaft 206 proximal of the intravascular device distal end 215. These distal portions of the sheath illustrate an original or resting state diameter of the sheath shaft 206. Portions of the sheath shaft 206 proximal to the intravascular device distal end 215 illustrate the sheath 200 in its expanded diameter state wherein the insertion of and presence of the intravascular device 214 within the sheath has forcibly expanded the elastomeric material of the sheath 200 to a larger inner diameter.

FIG. 7B illustrates a sectional view of the expandable introducer sheath 200 in a distal region without an intravascular device extending through that region. FIG. 7C illustrates a region of the sheath 200 in which the intravascular device 214 extends through the sheath shaft 206 and has caused the walls of the sheath shaft 206 to stretch and expand about the outer diameter of the intravascular device 214. The rib 207 abuts against an outer wall of the intravascular device 214 thereby providing extra spacing between an inner wall of the sheath shaft 206 and an outer wall of the intravascular device 214. This spacing or opening permits blood-pressure monitoring, blood removal, blood delivery, or drug infusion through the sheath via the hub 208. Although only one rib is shown in the figures, several ribs (the ribs being spaced apart radially) may extend longitudinally along an inner wall of the sheath shaft 206 to provide additional spacing between an outer wall of the intravascular device and an inner wall of the sheath shaft 206.

If desired, the sheath 200 can be reduced to its original smaller diameter state by simply removing the larger intravascular device 214 which allows the sheath shaft 206 to contract back to its original diameter by virtue of the elastomeric material characteristics. This permits the use of a smaller size sheath if desired after the use of the sheath in its expanded diameter state. However, the introduction of the larger intravascular device 214 causing expansion of the sheath 200 typically expands the opening through the wall of the vessel 56. Accordingly, when the intravascular device 214 is removed and the sheath 200 contracts back to its smaller original diameter, blood may flow through the puncture site 56 around the sheath.

To diminish any "backflow" of blood in this manner, an elongate solid rod-type dilator may be placed within the sheath to maintain expansion of the larger diameter size of the sheath to prevent such blood flow. However, the rod-type dilator is preferably "stepped" i.e., tapered, to have larger diameters at its proximal end and smaller diameters at its distal portions. Once fully inserted, the rod dilator maintains the sheath 200 in its larger expanded diameter state and then as the rod dilator is gradually removed proximally from the sheath and the smaller diameter portions of the rod dilator pass by the puncture site of the skin tissue 52, the opening of the vessel wall is permitted to gradually viscoelastically recover and retighten. This diminishes the amount of blood flow exiting the vessel around the outer diameter of the sheath 200 and because the rod dilator is solid, blood flow through the sheath 200 is prevented. Accordingly, the use of a tapered diameter rod dilator, or "stepwise" tapered rod dilator, increases the possibility of allowing a hole in the vessel to recover and effectively seal about the original diameter of the sheath shaft once the rod dilator is fully removed from the sheath. For example, the puncture size in the vessel that must be occluded after removal of the introducer sheath 200 would be 6 French (by using the "step" rod dilator) instead of 9 or 10 French. This smaller puncture size potentially reduces hematoma formation following removal of the sheath 200.

However, the sixth expandable introducer sheath 200 is not limited to use with a "step" rod dilator. Alternatively, a uniform diameter rod dilator may be used to maintain the sheath 200 in an expanded state to prevent blood flow around the sheath through the puncture site 56. The uniform rod dilator preferably would have an outer diameter equal to the largest intravascular device previously extending through the sheath 200. As in the use of the "stepped" rod dilator, a conventional procedure to occlude the puncture site would be used following removal of the sheath 200 from the vessel.

The sheath 200 should be lubricously coated (by silicone or hydrophylic lubrication) on its inner surface and outer surface to permit smooth movement of any intravascular devices relative to the sheath. As an example, the sheath 200 and its original diameter size (i.e., the portions distal of the intravascular device distal end 215 as shown in FIG. 7A) would be a size 6 French diameter. Portions of the sheath 200 proximal of the intravascular device end 215 as shown in FIG. 7A could be 7, 8, or 9 size French diameter depending upon the outer diameter of the intravascular device 214 inserted within the sheath.

In addition, a longitudnal stiffening member such as an elongate wire may be embedded in a wall of the sheath 200 or within a rib on the inner wall of the sheath 200. The stiffening member would extend a substantial portion of the length of the sheath 200. The stiffening member would provide additional support to prevent potential elongation of the sheath 200 when attempting to push a guide catheter (or other intravascular device) through the sheath 200. The potential for elongation of the sheath 200 occurs because of the friction caused between the outer surface of the guide catheter and the inner surface of the sheath 200 when the guide catheter is pushed through the sheath 200. The stiff- ening member would be incorporated into a sheath 200 in addition to the lubricous coating when the lubricous coating on the sheath 200 alone does not sufficiently reduce the friction between the guide catheter and the sheath 200.

III. Conclusion

The expandable introducer sheath of the present invention facilitates convenient percutaneous insertion and removal of multi-sized intravascular devices. The sheath can be expanded without having to perform a second percutaneous insertion technique to provide an expanded inner diameter sheath within the vessel and while maintaining a sheath within the vessel. This avoids re-traumatizing the vessel wall and skin tissue at the insertion site by avoiding the need to re-puncture the skin tissue and vessel wall either in the same location or in a second location. The inventive sheath in all embodiments is of simple tubular construction having a continuous wall surface and being free of any longitudinal slits along its length and hub region. This increases the ease of handling the sheath and accentuates management of blood flow. The lack of any slits or long free edges having corners reduces the chance of inadvertently dissecting the vessel wall.

Although the present invention has been described with reference to preferred embodiments, workers skilled in the art will recognize that changes may be made in form and detail without departing from the spirit and scope of the invention.

What is claimed is:

1. A sheath system for introducing intravascular devices percutaneously, the sheath system comprising:

an elongate flexible tubular member for placement within a vessel to slidably receive intravascular devices, the tubular member comprising a polymer material and including a wall having a continuous outer surface and a first inner diameter capable of slidably receiving intravascular devices therethrough and capable of being selectively expanded to a second, larger inner diameter while within the vessel and being maintained in the second larger inner diameter in a substantially uniform tubular shape without an additional member extending through the tubular member.

2. The sheath system of claim 1 wherein the tubular member further comprises:

a longitudinal fold formed in the wall of the tubular member extending along a portion of the length of the member and the fold being laid over onto the outer surface of wall of the tubular member, the fold capable of being unfolded to yield the second larger inner diameter of the tubular member.

3. The sheath system of claim 2 wherein the means for forcibly expanding further comprises:

an elongate mandrel insertable into the tubular member and having an outer diameter greater than the inner diameter of the tubular member when the fold is laid over onto the wall of the tubular member.

4. The sheath system of claim 3 wherein the mandrel comprises a guide catheter.

5. The sheath system of claim 1 and further comprising:

means for forcibly expanding the tubular member from its first inner diameter to its second larger inner diameter while a portion of the tubular member is in the vessel.

6. The sheath system of claim 1 wherein the polymer material of the tubular member further comprises:

a shape memory polymer material having a glass transition temperature greater than human body temperature wherein the tubular member is capable of being forcibly expanded from the first inner diameter to the second larger inner diameter when the shape memory polymer material is heated above the glass transition temperature and is capable of retaining the second larger inner diameter when the shape memory polymer material is cooled below the glass transition temperature while being forcibly expanded.

7. The sheath system of claim 6 and further comprising:

an elongate mandrel insertable into the tubular member and having an outer diameter greater than the first inner diameter of the tubular member, the mandrel having a heating element disposed on a distal portion of the mandrel and being capable of heating portions of the tubular member adjacent the heating element to exceed the glass transition temperature of the shape memory polymer material.

8. The sheath system of claim 6 wherein the shape memory polymer material is a polyurethane material with a tightly controlled glass transition temperature of about 45° C.

9. The sheath system of claim 6 wherein the tubular member is first formed having an inner diameter larger than the first inner diameter size and then mechanically manipulated to have the first inner diameter size.

10. The sheath system of claim 1 wherein the tubular member further comprises: a tubular braided material matrix embedded in the polymer material.

11. A sheath system for introducing intravascular devices percutaneously, the sheath system comprising:

an elongate flexible tubular member for placement within a vessel to slidably receive intravascular devices, the tubular member comprising a shape memory polymer and having a first inner diameter capable of being expanded to a second, larger inner diameter and being maintained in the second larger inner diameter in a substantially uniform tubular shape; and a mandrel having an outer diameter approximately equal to the second larger predetermined inner diameter and having a heated distal portion to heat the tubular member above a glass transition temperature of the shape memory polymer material to permit the outer diameter of the mandrel to forcibly expand the sheath to the second larger inner diameter and to cool the sheath below the glass transition temperature of the shape memory polymer with the mandrel within the tubular member so that the tubular member retains the second larger inner diameter.

12. A sheath for introducing intravascular devices percutaneously, the sheath comprising:

an elongate flexible tubular member for placement within a vessel to slidably receive intravascular devices, the tubular member comprising a shape memory polymer material having a glass transition temperature greater than human body temperature, and the tubular member having a first inner diameter capable of being selectively expanded to a second, larger inner diameter.

13. The sheath of claim 12 wherein the shape memory polymer material is a polyurethane material having a glass transition temperature of about 45° C.

14. A method of introducing intravascular devices percutaneously comprising:

providing an elongate flexible tubular sheath for slidably receiving intravascular catheters, the sheath being formed primarily of a polymer material and including a wall having a continuous outer surface and defining a first inner diameter;

inserting a distal end of the sheath into a vascular vessel with a proximal end of the sheath protruding proximally outward from the vessel; and applying a radial force to the wall of the sheath to expand the sheath to have a second inner diameter larger than the first inner diameter of the sheath wherein the second larger inner diameter is maintained without an additional member extending within the sheath.

15. The method of claim 14 wherein the providing step further comprises:

forming the sheath from a shape-memory polymer material.

16. The method of claim 15 wherein the step of applying force further comprises:

providing a mandrel having an outer diameter approximately equal to the second larger predetermined inner diameter and having a heated distal portion;

inserting the mandrel within the sheath to heat the sheath above a glass transition temperature of the shape memory polymer material to permit the outer diameter of the mandrel to forcibly expand the sheath to the second larger inner diameter; and cooling the sheath below the glass transition temperature of the shape memory polymer with the mandrel within the sheath so that the sheath retains the second larger inner diameter.

17. The method of claim 14 wherein the providing step further comprises:

forming the sheath from an alloy of an ester-based polyurethane material and an ester-based polyurethane material.

18. The method of claim 14 wherein the providing step further comprises:

extruding the sheath to have the second larger inner diameter;

shrinking the sheath to assume the first inner diameter;

placing a tubular sleeve over the shrunken sheath to maintain the first inner diameter size; and removing the sleeve from the sheath prior to insertion of the sheath within the vessel.

19. The method of claim 18 wherein the step of applying radial force further comprises:

providing a mandrel having an outer diameter approximately equal to the second larger inner diameter and having a heated distal portion;

inserting the mandrel within the sheath to heat the sheath above a glass transition temperature of the shape memory polymer material to permit the outer diameter of the mandrel to forcibly expand the sheath to the second larger inner diameter; and cooling the sheath below the glass transition temperature of the shape memory polymer with the mandrel within the sheath so that the sheath retains the second larger inner diameter.

20. The method of claim 14 wherein the sheath as initially provided has a longitudinal fold in a wall of the sheath extending along a portion of the length of the sheath, and wherein the step of applying radial force further comprises;

unfolding the fold in the sheath to expand the sheath so that the sheath has the second larger inner diameter that is greater than the first inner diameter of the sheath when folded.

21. The method of claim 20 wherein the unfolding step further comprises:

inserting a mandrel into the sheath to expand the sheath from the folded first inner diameter to the second larger unfolded inner diameter.

22. A sheath for introducing intravascular devices percutaneously, the sheath comprising:

an elongate flexible tubular member for placement within a vessel to slidably receive intravascular devices, the tubular member having a first inner diameter and comprising a shape memory polymer material having a glass transition temperature greater than human body temperature wherein the tubular member is capable of being forcibly expanded from the first inner diameter to a second larger inner diameter when the shape memory polymer material is heated above the glass transition temperature and is capable of retaining the second larger inner diameter when the shape memory polymer material is cooled below the glass transition temperature while being forcibly expanded.

23. The sheath of claim 22 wherein the shape memory polymer material is a polyurethane material with a tightly controlled glass transition temperature of about 45° C.

24. The sheath of claim 22 wherein the tubular member is first formed having an inner diameter larger than the first inner diameter size and then mechanically manipulated to have the first inner diameter size.

25. The sheath of claim 22 wherein the tubular member further comprises:

a tubular braided material matrix embedded in the shape memory polymer material.

26. A method of introducing intravascular devices percutaneously comprising:

providing an elongate flexible tubular sheath for slidably receiving intravascular catheters, the sheath being formed primarily ot a shape-memory polymer material and including a wall having a continuous outer surface and defining a first inner diameter;

inserting a distal end of the sheath into a vascular vessel with a proximal end of the sheath protruding proximally outward from the vessel;

providing a mandrel having an outer diameter approximately equal to a second larger predetermined inner diameter of the sheath and having a heated distal portion;

inserting the mandrel within the sheath to heat the sheath above a glass transition temperature of the shape memory polymer material to permit the outer diameter of the mandrel to forcibly expand the sheath to the second larger inner diameter; and cooling the sheath below the glass transition temperature of the shape memory polymer with the mandrel within the sheath so that the sheath retains the second larger inner diameter.

27. A sheath system for introducing intravascular devices percutaneously, the sheath comprising:

an elongate flexible tubular member for placement within a vessel to slidably receive intravascular devices, the tubular member comprising an elastomeric material with a substantially uniform wall thickness, having a wall with a continuous outer surface, and having a first inner diameter with a substantially uniform tubular shape capable of being selectively expanded to a second, larger inner diameter while within the vessel and having at least one rib extending longitudinally along an inner surface of the wall of the tubular member when the tubular member has the first inner diameter and when the tubular member has the second larger inner diameter.

28. The sheath system of claim 27 and further comprising:

an elongate flexible intravascular device adapted for insertion within the tubular member and having an outer diameter equal to the second larger inner diameter of the tubular member so that insertion of the intravascular device within the tubular member causes radial expansion of the tubular member to its second larger inner diameter and the rib on the inner surface of the wall maintaining spacing between the outer diameter of the intravascular device and the second inner diameter of the tubular member.

29. A sheath system for introducing intravascular devices percutaneously, the sheath system comprising:

an elongate flexible tubular member for placement within a vessel to slidably receive intravascular devices, the tubular member comprising a tubular hub and a tubular shaft extending from the hub, the shaft member comprising a polymeric material and including a wall having a continuous outer surface and having a first inner diameter capable of slidably receiving intravascular devices therethrough and capable of being selectively expanded to a second, larger inner diameter while within the vessel and being maintained in the second larger inner diameter in a substantially uniform tubular shape without an additional member extending through the tubular member, wherein the hub has an inner diameter at least as large as the second inner diameter of the shaft.

30. A sheath for introducing intravascular devices percutaneously, the sheath comprising:

an elongate flexible tubular member for placement within a vessel to slidably receive intravascular devices, the tubular member including a proximal hub portion and a distal shaft portion extending from the hub portion, the distal shaft portion comprising a shape memory polymer material having a glass transition temperature greater than human body temperature, and the tubular member having a first inner diameter capable of being selectively expanded to a second, larger inner diameter, wherein the proximal hub portion has an inner diameter at least as large as the second inner diameter of the distal shaft portion.

* * * * *

UNITED STATES PATENT AND TRADEMARK OFFICE
CERTIFICATE OF CORRECTION

PATENT NO. : 6,090,072
DATED : JULY 18, 2000
INVENTOR(S) : WILLIAM F. KRATOSKA ET AL.

It is certified that error appears in the above-identified patent and that said Letters Patent is hereby corrected as shown below:

Col. 29, line 31, delete "ot", insert -- of --

Signed and Sealed this

Twenty-second Day of May, 2001

Attest:

NICHOLAS P. GODICI

*Attesting Officer*  *Acting Director of the United States Patent and Trademark Office*